US012343256B2

(12) United States Patent
Christianson et al.

(10) Patent No.: US 12,343,256 B2
(45) Date of Patent: Jul. 1, 2025

(54) ANCHOR HOOK FOR SIDE-DELIVERY TRANSCATHETER HEART VALVE PROSTHESIS

(71) Applicant: VDyne, Inc., Maple Grove, MN (US)

(72) Inventors: Mark Christianson, Plymouth, MN (US); Robert Vidlund, Forest Lake, MN (US); Chad Perrin, Andover, MN (US); Craig Ekvall, East Bethel, MN (US)

(73) Assignee: VDyne, Inc., Maple Grove, MN (US)

( * ) Notice: Subject to any disclaimer, the term of this patent is extended or adjusted under 35 U.S.C. 154(b) by 863 days.

(21) Appl. No.: 17/372,022

(22) Filed: Jul. 9, 2021

(65) Prior Publication Data
US 2021/0330459 A1 Oct. 28, 2021

Related U.S. Application Data

(63) Continuation of application No. PCT/US2020/013240, filed on Jan. 11, 2020.
(Continued)

(51) Int. Cl.
*A61F 2/24* (2006.01)
*A61B 17/00* (2006.01)
(Continued)

(52) U.S. Cl.
CPC ........ *A61F 2/2436* (2013.01); *A61B 17/3468* (2013.01); *A61F 2/2418* (2013.01);
(Continued)

(58) Field of Classification Search
CPC ........ A61F 2/2436; A61F 2/2418; A61F 2/91; A61F 2210/0014; A61F 2220/0016;
(Continued)

(56) References Cited

U.S. PATENT DOCUMENTS 3,744,060 A 7/1973 Bellhouse et al.
4,079,468 A 3/1978 Liotta et al.
(Continued)

FOREIGN PATENT DOCUMENTS

AU 2006203686 B2 11/2008
AU 2009219415 A1 9/2009
(Continued)

OTHER PUBLICATIONS

International Search Report and Written Opinion for International Application No. PCT/US2023/076845 dated Mar. 4, 2024, 10 pages.
(Continued)

*Primary Examiner* — Jerrah Edwards
*Assistant Examiner* — Jose H. Trevino, III

(57) ABSTRACT

The invention relates to an anchor hook and methods of using the same for subannular anchoring of a transcatheter heart valve replacement, and in particular for an orthogonally delivered (side-delivered) transcatheter prosthetic heart valve having a annular support frame having compressible wire cells that facilitate rolling and folding the valve length-wise, or orthogonally to the central axis of the flow control component, allowing a very large diameter valve to be delivered and deployed to the mitral or tricuspid valve from the inferior vena cava or superior vena cava, or trans-septally to the mitral valve, the valve having a height of about 5-60 mm and a diameter of about 25-80 mm, without requiring an oversized diameter catheter and without requiring a delivery catheter to bend 90 degrees during deployment.

9 Claims, 33 Drawing Sheets

Related U.S. Application Data

(60) Provisional application No. 62/847,741, filed on May 14, 2019, provisional application No. 62/790,465, filed on Jan. 10, 2019.

(51) Int. Cl.
*A61B 17/34* (2006.01)
*A61F 2/91* (2013.01)

(52) U.S. Cl.
CPC .............. *A61B 2017/00243* (2013.01); *A61B 2017/00292* (2013.01); *A61B 2017/00358* (2013.01); *A61F 2/91* (2013.01); *A61F 2210/0014* (2013.01); *A61F 2220/0016* (2013.01); *A61F 2230/0017* (2013.01); *A61F 2250/0098* (2013.01)

(58) Field of Classification Search
CPC ..... A61F 2230/0017; A61F 2250/0098; A61B 17/3468; A61B 2017/00243; A61B 2017/00292; A61B 2017/00358; A61B 17/064; A61B 2017/0647
See application file for complete search history.

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |
| 5,554,185 A | 9/1996 | Block et al. |
| 5,800,531 A | 9/1998 | Cosgrove et al. |
| 5,906,642 A | 5/1999 | Caudillo et al. |
| 6,006,134 A | 12/1999 | Hill et al. |
| 6,197,013 B1 | 3/2001 | Reed et al. |
| 6,290,719 B1 | 9/2001 | Garberoglio |
| 6,312,464 B1 | 11/2001 | Navia |
| 6,449,507 B1 | 9/2002 | Hill et al. |
| 6,458,153 B1 | 10/2002 | Bailey et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,074,189 B1 | 7/2006 | Montegrande |
| 7,125,418 B2 | 10/2006 | Duran et al. |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,361,189 B2 | 4/2008 | Case et al. |
| 7,374,571 B2 | 5/2008 | Pease et al. |
| 7,442,204 B2 | 10/2008 | Schwammenthal et al. |
| 7,449,027 B2 | 11/2008 | Hunt et al. |
| 7,621,948 B2 | 11/2009 | Herrmann et al. |
| 7,648,527 B2 | 1/2010 | Agnew |
| 7,717,952 B2 | 5/2010 | Case et al. |
| 7,749,245 B2 | 7/2010 | Cohn et al. |
| 7,753,949 B2 | 7/2010 | Lamphere |
| 7,811,316 B2 | 10/2010 | Kalmann et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,628,571 B1 | 1/2014 | Hacohen et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 8,998,982 B2 | 4/2015 | Richter et al. |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,402,720 B2 | 8/2016 | Richter et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,504,562 B2 | 11/2016 | Richter et al. |
| 9,510,941 B2 | 12/2016 | Bishop et al. |
| 9,526,613 B2 | 12/2016 | Gross et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,597,181 B2 | 3/2017 | Christianson et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello et al. |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |

(56) References Cited

U.S. PATENT DOCUMENTS

| | | |
|---|---|---|
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |
| 10,080,653 B2 | 9/2018 | Conklin et al. |
| 10,085,834 B2 | 10/2018 | Benson et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson et al. |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,662 B2 | 11/2019 | Alkhatib |
| 10,485,976 B2 | 11/2019 | Streeter et al. |
| 10,517,718 B2 | 12/2019 | Richter et al. |
| 10,537,425 B2 | 1/2020 | Richter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,653,523 B2 | 5/2020 | Chambers et al. |
| 10,758,346 B1 | 9/2020 | Christianson et al. |
| 10,761,511 B2 | 9/2020 | Chen et al. |
| 10,779,937 B2 | 9/2020 | Vidlund et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund, I et al. |
| 11,173,027 B2 | 11/2021 | Christianson et al. |
| 11,179,239 B2 | 11/2021 | Vidlund et al. |
| 11,185,409 B2 | 11/2021 | Christianson et al. |
| 11,202,706 B2 | 12/2021 | Christianson et al. |
| 11,234,812 B2 | 2/2022 | Green et al. |
| 11,234,813 B2 | 2/2022 | Perrin |
| 11,253,359 B2 | 2/2022 | Vidlund et al. |
| 11,273,032 B2 | 3/2022 | Christianson et al. |
| 11,273,033 B2 | 3/2022 | Christianson et al. |
| 11,278,437 B2 | 3/2022 | Christianson et al. |
| 11,298,227 B2 | 4/2022 | Vidlund et al. |
| 11,331,186 B2 | 5/2022 | Christianson et al. |
| 11,337,807 B2 | 5/2022 | Christianson et al. |
| 11,344,412 B2 | 5/2022 | Vidlund et al. |
| 11,344,413 B2 | 5/2022 | Christianson et al. |
| 11,712,335 B2 | 8/2023 | Christianson et al. |
| 11,717,399 B2 | 8/2023 | Armer et al. |
| 11,786,366 B2 | 10/2023 | Vidlund et al. |
| 2002/0138138 A1 | 9/2002 | Yang |
| 2002/0183827 A1 | 12/2002 | Derus et al. |
| 2003/0040772 A1 | 2/2003 | Hyodoh et al. |
| 2003/0040808 A1 | 2/2003 | Stack et al. |
| 2003/0055495 A1 | 3/2003 | Pease et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0117009 A1 | 6/2004 | Cali et al. |
| 2004/0167619 A1 | 8/2004 | Case et al. |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0203614 A1 | 9/2005 | Forster et al. |
| 2005/0228472 A1 | 10/2005 | Case et al. |
| 2005/0228495 A1 | 10/2005 | Macoviak |
| 2006/0015167 A1 | 1/2006 | Armstrong et al. |
| 2006/0173524 A1 | 8/2006 | Salahieh et al. |
| 2006/0190075 A1 | 8/2006 | Jordan et al. |
| 2006/0195180 A1 | 8/2006 | Kheradvar et al. |
| 2006/0195183 A1 | 8/2006 | Navia et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0073387 A1 | 3/2007 | Forster et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0048656 A1 | 2/2009 | Wen |
| 2009/0054976 A1 | 2/2009 | Tuval et al. |
| 2009/0094189 A1 | 4/2009 | Stephens |
| 2009/0132035 A1 | 5/2009 | Roth et al. |
| 2009/0164003 A1 | 6/2009 | Kheradvar |
| 2009/0192586 A1 | 7/2009 | Tabor et al. |
| 2009/0192601 A1 | 7/2009 | Rafiee et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |

(56) References Cited

U.S. PATENT DOCUMENTS

| | | |
|---|---|---|
| 2010/0016894 A1* | 1/2010 | Houard .............. A61B 17/0401 |
| | | 606/232 |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0185275 A1 | 7/2010 | Richter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0160836 A1 | 6/2011 | Behan |
| 2011/0172764 A1 | 7/2011 | Badhwar |
| 2011/0172784 A1 | 7/2011 | Richter et al. |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2011/0319989 A1 | 12/2011 | Lane et al. |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0035719 A1 | 2/2012 | Forster et al. |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0046373 A1 | 2/2013 | Cartledge et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0178931 A1 | 7/2013 | Fargahi |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | Mclean et al. |
| 2013/0325110 A1 | 12/2013 | Khalil et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0025164 A1 | 1/2014 | Montorfano et al. |
| 2014/0031924 A1 | 1/2014 | Bruchman et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0067037 A1 | 3/2014 | Fargahi |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0172077 A1 | 6/2014 | Bruchman et al. |
| 2014/0172083 A1 | 6/2014 | Bruchman et al. |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0249621 A1 | 9/2014 | Eidenschink |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1* | 9/2014 | Kovach .............. A61B 17/1227 |
| | | 606/151 |
| 2014/0277342 A1 | 9/2014 | Roeder et al. |
| 2014/0277388 A1 | 9/2014 | Skemp |
| 2014/0277408 A1 | 9/2014 | Folan |
| 2014/0277563 A1 | 9/2014 | White |
| 2014/0288480 A1 | 9/2014 | Zimmerman et al. |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119978 A1 | 4/2015 | Tegels et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173897 A1 | 6/2015 | Raanani et al. |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |

(56) References Cited

U.S. PATENT DOCUMENTS

| | | |
|---|---|---|
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220363 A1 | 8/2016 | Peter |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235525 A1 | 8/2016 | Rothstein et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0302921 A1 | 10/2016 | Gosal et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056163 A1 | 3/2017 | Tayeb et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100236 A1 | 4/2017 | Robertson et al. |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143446 A1 | 5/2017 | Kölbel |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0319333 A1 | 11/2017 | Tegels et al. |
| 2017/0325943 A1 | 11/2017 | Robin et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0000586 A1 | 1/2018 | Ganesan et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042721 A1 | 2/2018 | Chambers |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0098847 A1 | 4/2018 | Tuseth et al. |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |

(56) References Cited

U.S. PATENT DOCUMENTS

| | | |
|---|---|---|
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | Mclean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318071 A1 | 11/2018 | Lozonschi et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0333259 A1 | 11/2018 | Dibie |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008636 A1 | 1/2019 | Francis et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0321171 A1 | 10/2019 | Morriss et al. |
| 2019/0365538 A1 | 12/2019 | Chambers et al. |
| 2019/0388219 A1 | 12/2019 | Lane et al. |
| 2020/0008941 A1 | 1/2020 | Stappenbeck et al. |
| 2020/0093589 A1 | 3/2020 | Christianson et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154010 A1 | 5/2021 | Schneider et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0353412 A1 | 11/2021 | Christianson et al. |
| 2021/0401572 A1 | 12/2021 | Nasr et al. |

(56) References Cited

U.S. PATENT DOCUMENTS

| | | | |
|---|---|---|---|
| 2022/0000614 A1 | 1/2022 | Vidlund et al. | |
| 2022/0087815 A1 | 3/2022 | Bernshtein et al. | |
| 2022/0096226 A1 | 3/2022 | Christianson et al. | |
| 2022/0160504 A1 | 5/2022 | Vidlund et al. | |
| 2022/0249228 A1 | 8/2022 | Vidlund et al. | |
| 2022/0280292 A1 | 9/2022 | Vidlund et al. | |
| 2022/0280296 A1 | 9/2022 | Christianson et al. | |
| 2022/0296369 A1 | 9/2022 | Kheradvar et al. | |
| 2022/0323212 A1 | 10/2022 | Vidlund et al. | |
| 2022/0338978 A1 | 10/2022 | Yushtein | |
| 2022/0370198 A1 | 11/2022 | Nir et al. | |
| 2022/0378410 A1* | 12/2022 | Hacohen | A61B 17/0401 |
| 2022/0387174 A1 | 12/2022 | Schwarcz et al. | |
| 2022/0395370 A1 | 12/2022 | Vidlund et al. | |
| 2022/0409369 A1 | 12/2022 | Christianson et al. | |
| 2023/0157816 A1 | 5/2023 | Perrin | |
| 2023/0172710 A1 | 6/2023 | Nir | |
| 2023/0190463 A1 | 6/2023 | Nir | |
| 2023/0200990 A1 | 6/2023 | Chen et al. | |
| 2023/0263630 A1 | 8/2023 | Saar et al. | |
| 2023/0338140 A1 | 10/2023 | Cartledge et al. | |
| 2024/0074855 A1 | 3/2024 | Atias et al. | |
| 2024/0138983 A1 | 5/2024 | Ekvall et al. | |
| 2024/0148496 A1 | 5/2024 | Christianson | |
| 2024/0148497 A1 | 5/2024 | Bukin et al. | |
| 2024/0225828 A1 | 7/2024 | Vidlund et al. | |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 A | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 B | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920862 A | 4/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |

(56) References Cited

FOREIGN PATENT DOCUMENTS

| | | |
|---|---|---|
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| EP | 3897462 A1 | 10/2021 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010508093 A | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013517011 A | 5/2013 |

(56) References Cited

FOREIGN PATENT DOCUMENTS

| | | | |
|---|---|---|---|
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2014528761 A | 10/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008055301 A1 | 5/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010079427 A1 | 7/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016183523 A1 | 11/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017123802 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |

(56) References Cited

FOREIGN PATENT DOCUMENTS

| | | |
|---|---|---|
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018136726 A1 | 7/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |
| WO | WO-2020061124 A1 | 3/2020 |
| WO | WO-2020061331 A2 | 3/2020 |
| WO | WO-2020131978 A1 | 6/2020 |
| WO | WO-2020154735 A1 | 7/2020 |
| WO | WO-2020181154 A2 | 9/2020 |
| WO | WO-2020186251 A1 | 9/2020 |
| WO | WO-2020227249 A1 | 11/2020 |
| WO | WO-2021035032 A1 | 2/2021 |
| WO | WO-2021040996 A1 | 3/2021 |
| WO | WO-2021146515 A1 | 7/2021 |
| WO | WO-2022010974 A1 | 1/2022 |
| WO | WO-2023164489 A2 | 8/2023 |
| WO | WO-2024081883 A1 | 4/2024 |

OTHER PUBLICATIONS

Non-Final Office Action for U.S. Appl. No. 17/526,691 dated Mar. 11, 2024, 9 pages.
Office Action and Search report for Chinese Application No. CN201980075586.9 dated Feb. 5, 2024, 15 pages.
Office Action for Canadian Application No. CA3152042 dated Feb. 20, 2024, 5 pages.
Office Action for Canadian Patent Application No. CA20203152632 dated Feb. 19, 2024, 4 pages.
Office Action for Canadian Patent Application No. CA3113429 dated Feb. 13, 2024, 4 pages.
Office Action for European Application No. EP20200801681 dated Dec. 11, 2023, 7 pages.
Office Action for Japanese Application No. JP20210563105 mailed Feb. 26, 2024, 8 pages.
Office Action for Japanese Patent Application No. JP20210555207 dated Jan. 31, 2024, 6 pages.
Office Action for Japanese Patent Application No. JP2021547343 dated Jan. 31, 2024, 6 pages.
International Search Report and Written Opinion for International Application No. PCT/US2019/028822, mailed Oct. 24, 2019, 14 pages.
Office Action for U.S. Appl. No. 16/435,687, mailed Aug. 7, 2019, 19 pages.
International Search Report and Written Opinion for International Application No. PCT/US2019/051615, mailed Mar. 2, 2020, 14 pages.
Office Action for U.S. Appl. No. 17/167,983, mailed Apr. 13, 2021, 20 pages.
International Search Report and Written Opinion for International Application No. PCT/US2019/051957, mailed Apr. 30, 2020, 16 pages.
Office Action for U.S. Appl. No. 16/155,890, mailed Feb. 8, 2019, 13 pages.
Office Action for U.S. Appl. No. 16/448,108, mailed Jan. 21, 2020, 14 pages.
Office Action for U.S. Appl. No. 16/448,108, mailed Sep. 1, 2020, 14 pages.
Office Action for U.S. Appl. No. 16/448,108, mailed Mar. 8, 2021, 8 pages.

(56) References Cited

OTHER PUBLICATIONS

Office Action for U.S. Appl. No. 16/163,577, mailed Mar. 8, 2021, 10 pages.
Office Action for U.S. Appl. No. 16/455,417, mailed Sep. 23, 2019, 11 pages.
International Search Report and Written Opinion for International Application No. PCT/US2019/067010, mailed Mar. 10, 2020, 17 pages.
Office Action for U.S. Appl. No. 17/221,547, mailed Aug. 4, 2021, 11 pages.
Office Action for U.S. Appl. No. 16/455,740, mailed Jul. 24, 2020, 7 pages.
International Search Report and Written Opinion for International Application No. PCT/US2020/015231, mailed Apr. 23, 2020, 10 pages.
International Search Report and Written Opinion for International Application No. PCT/US2020/021300, mailed Oct. 7, 2020, 6 pages.
Office Action for U.S. Appl. No. 17/236,219, mailed Aug. 4, 2021, 17 pages.
International Search Report and Written Opinion for International Application No. PCT/US2020/031390, mailed Aug. 3, 2020, 10 pages.
International Search Report and Written Opinion for International Application No. PCT/US2020/013240, mailed Jun. 3, 2020, 7 pages.
International Search Report and Written Opinion for International Application No. PCT/US2020/022828, mailed May 19, 2020, 12 pages.
Office Action for U.S. Appl. No. 17/154,227, mailed Mar. 29, 2021, 6 pages.
Office Action for U.S. Appl. No. 17/154,227, mailed Jun. 18, 2021, 8 pages.
Office Action for U.S. Appl. No. 16/442,504, mailed Jan. 14, 2020, 11 pages.
Office Action for U.S. Appl. No. 16/445,210, mailed Jan. 28, 2021, 7 pages.
Office Action for U.S. Appl. No. 17/154,438, mailed May 3, 2021, 16 pages.
International Search Report and Written Opinion for International Application No. PCT/US2021/013570, mailed Apr. 1, 2021, 9 pages.
International Search Report and Written Opinion for International Application No. PCT/US2020/045195, mailed Jan. 8, 2021, 18 pages.
Office Action for U.S. Appl. No. 17/193,936, mailed May 27, 2021, 6 pages.
International Search Report and Written Opinion for International Application No. PCT/US2020/047162, mailed Dec. 30, 2020, 9 pages.
Extended European Search Report for European Application No. 19863898.3, mailed Apr. 29, 2022, 13 pages.
Extended European Search Report for European Application No. 19897707.6, mailed Sep. 6, 2022, 7 pages.
Extended European Search Report for European Application No. 20745513.0, mailed Sep. 20, 2022, 9 pages.
Extended European Search Report for European Application No. 20767325.2, mailed on Oct. 25, 2022, 5 pages.
Extended European Search Report for European Application No. 20769769.9, mailed Oct. 17, 2022, 6 pages.
Extended European Search Report for European Application No. 20801681.6, mailed Jan. 18, 2023, 13 pages.
Office Action for U.S. Appl. No. 16/443,862, mailed Nov. 12, 2021, 9 pages.
Office Action for U.S. Appl. No. 16/449,420, mailed Sep. 1, 2021, 16 pages.
Office Action for U.S. Appl. No. 16/711,415, mailed Jan. 18, 2022, 7 pages.
Office Action for U.S. Appl. No. 17/062,080, mailed Dec. 15, 2022, 14 pages.
Office Action for U.S. Appl. No. 17/167,988, mailed Sep. 22, 2021, 19 pages.
Office Action for U.S. Appl. No. 17/221,547, mailed Oct. 21, 2021, 9 pages.
Office Action for U.S. Appl. No. 17/222,182, mailed Sep. 2, 2021, 23 pages.
Office Action for U.S. Appl. No. 17/222,430, mailed Oct. 7, 2021, 17 pages.
Office Action for U.S. Appl. No. 17/388,983, mailed Jan. 6, 2022, 11 pages.
Extended European Search Report for European Application No. EP20854535 dated Jun. 23, 2023, 8 pages.
Office Action for U.S. Appl. No. 17/666,086 dated Jul. 5, 2023, 16 pages.
Office Action for European Application No. 19863898.3 dated Mar. 24, 2023, 6 pages.
Invitation to Pay Additional Fees for International Application No. PCT/US2023/63044, mailed Jul. 31, 2023, 2 pages.
Extended European Search Report for European Application No. EP20856704 dated Aug. 22, 2023, 11 pages.
International Search Report and Written Opinion for PCT Application No. PCT/US2023/063044 dated Oct. 24, 2023, 13 pages.
Office Action European Application No. 19863898.3 mailed Nov. 27, 2023, 4 pages.
Office Action for European Application No. 20769769.9 dated Sep. 8, 2023, 4 pages.
Office Action for Japanese Application No. JP20210516666 dated Aug. 31, 2023, 19 pages.
Office Action for Japanese Application No. JP20210535023 dated Oct. 27, 2023, 17 pages.
Office Action for U.S. Appl. No. 17/207,076 dated Aug. 17, 2023, 6 pages.
Office Action for Australian Application No. 2019342130 mailed May 22, 2024, 3 pages.
Office Action for Chinese Application No. 201980090378.6, with Search Report, mailed Mar. 12, 2024, 28 pages, English translation included.
Office Action for Chinese Application No. 202080074543.1, with Search Report, mailed Mar. 28, 2024, 18 pages, English translation included.
Office Action for Japanese Application No. 2021-516666 mailed Apr. 22, 2024, 6 pages, English translation included.
Office Action for Japanese Application No. 2021-535023 mailed Apr. 22, 2024, 4 pages, English translation included.
Office Action for Japanese Application No. 2021-547343 mailed May 13, 2024, 4 pages, English translation included.
Office Action for Japanese Application No. 2022-511360 mailed Apr. 18, 2024, 6 pages, English translation included.
Office Action for Japanese Application No. 2022-513172 mailed Apr. 18, 2024, 12 pages, English translation included.
Office Action for U.S. Appl. No. 17/707,493 mailed Mar. 29, 2024, 21 pages.
Office Action for U.S. Appl. No. 18/410,230, mailed Jun. 4, 2024, 11 pages.
Invitation to Pay Additional Fees for International Application No. PCT/US2024/035388, mailed Sep. 17, 2024, 3 pages.
Office Action for Australian Application No. 2019406832 mailed Jul. 26, 2024, 4 pages.
Office Action for Australian Application No. 2020231221 mailed Sep. 11, 2024, 4 pages.
Office Action for Australian Application No. 2020239265 mailed Sep. 2, 2024, 3 pages.
Office Action for European Application No. 20801681.6 mailed Jul. 31, 2024, 5 pages.
Office Action for U.S. Appl. No. 17/682,875, mailed Sep. 28, 2024, 18 pages.
Office Action for U.S. Appl. No. 17/825,551, mailed Aug. 29, 2024, 11 pages.
Office Action for U.S. Appl. No. 18/329,098, mailed Oct. 24, 2024, 12 pages.
Extended European Search Report for European Application No. 23215329.6, mailed on Jul. 5, 2024, 5 pages.

(56) References Cited

OTHER PUBLICATIONS

Office Action for European Application No. 20856704.0 mailed Jul. 29, 2024, 4 pages.
Office Action for U.S. Appl. No. 17/707,493 mailed Jul. 8, 2024, 9 pages.

* cited by examiner

FIG. 28  FIG. 29  FIG. 30
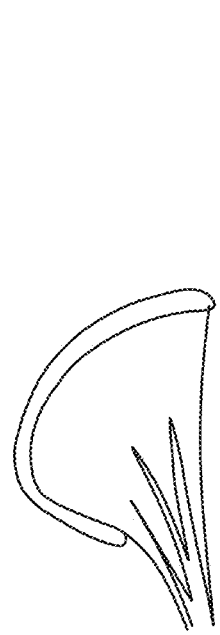
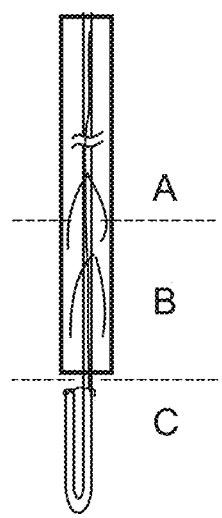
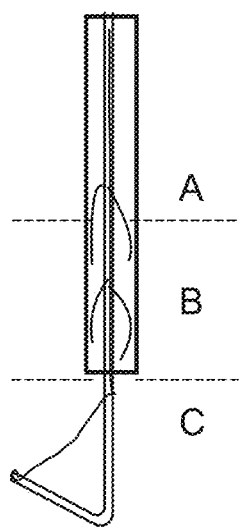
FIG. 31  FIG. 32
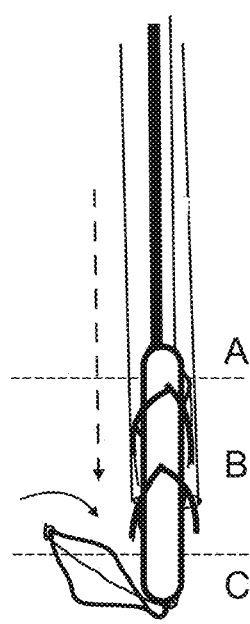
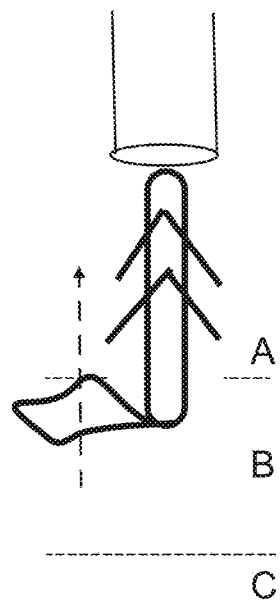

θ = 20-100° anchor delivery
catheter
push/pull guide wire
anchor channel/
pocket
anchor shaft
anchor tabs/barbs
anchor hook
catheter nosecone FIG. 43
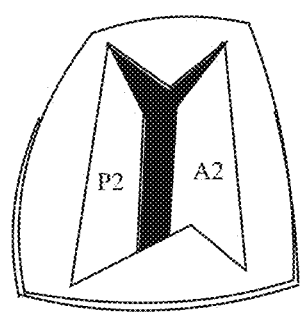
FIG. 44
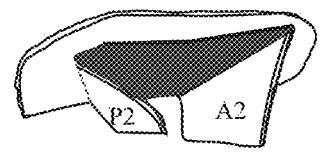
FIG. 45
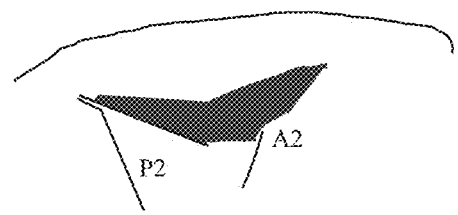
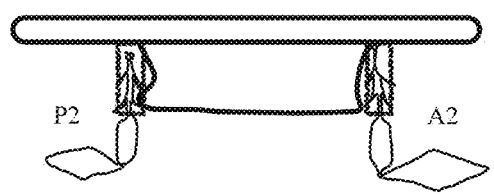
channels on external
surface of valve body
FIG. 46
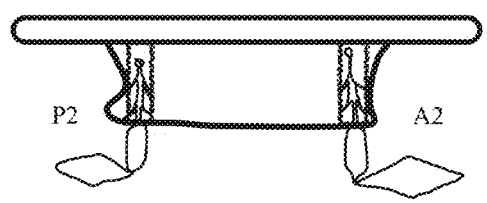
channels within
cylinder of valve body
FIG. 47 view from above three anchors four anchors

FIG. 85A
FIG. 85B
FIG. 85C
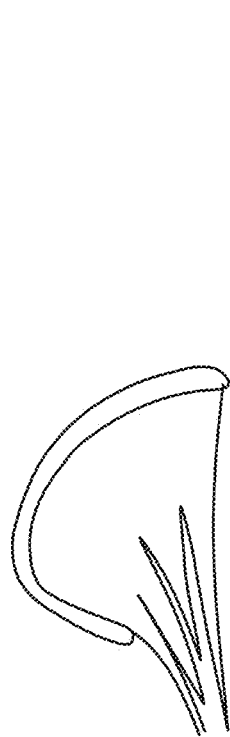
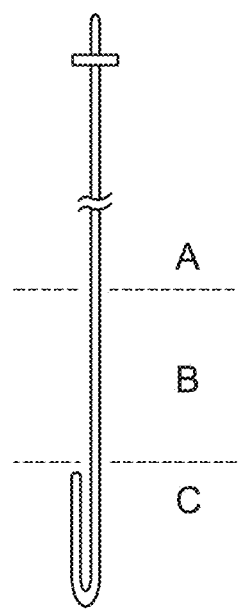
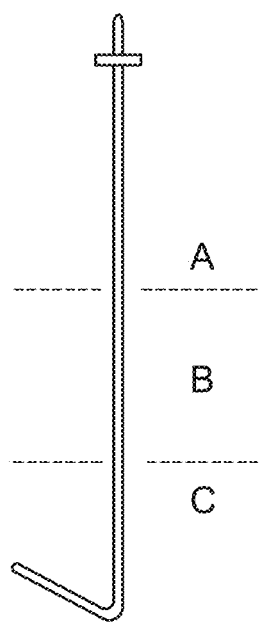
FIG. 85D
FIG. 85E
FIG. 85F
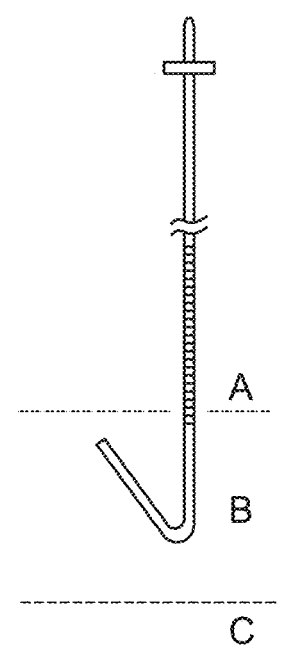
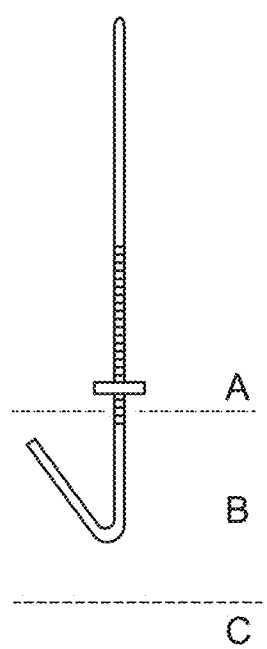
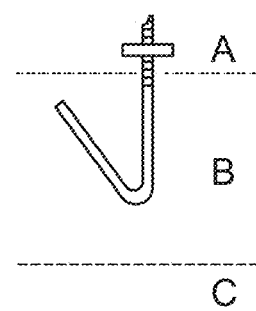

ANCHOR HOOK FOR SIDE-DELIVERY TRANSCATHETER HEART VALVE PROSTHESIS

CROSS-REFERENCE TO RELATED APPLICATIONS

This application is a continuation of International Application No. PCT/US2020/013240, filed Jan. 11, 2020, entitled "Anchor Hook for Side-Delivery Transcatheter Heart Valve Prosthesis," which claims priority to and the benefit of U.S. Provisional Application Ser. No. 62/790,465, entitled "Subannular Securement Anchors for Orthogonal Transcatheter Heart Valve Prosthesis," filed Jan. 10, 2019 and U.S. Provisional Application Ser. No. 62/847,741, entitled "Retrievable Anchor Hook for Side-Delivery Transcatheter Heart Valve Prosthesis," filed May 14, 2019, the disclosure of each of which is incorporated herein by reference in its entirety.

BACKGROUND OF THE INVENTION

Field of the Invention

The invention relates to an anchor hook and methods of using the same for subannular anchoring of a transcatheter heart valve replacement (A61F2/2412).

Description of the Related Art

Embodiments are described herein that relate to prosthetic heart valves, and devices and methods for use in the delivery and deployment of such valves.

Prosthetic heart valves can pose challenges for delivery and deployment within a heart, particularly for delivery by catheters through the patient's vasculature rather than through a surgical approach.

Delivery of traditional transcatheter prosthetic valves generally includes compressing the valve in a radial direction and loading the valve into a delivery catheter such that a central annular axis of the valve is parallel to the lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space).

Accordingly, a need exists for prosthetic valves with one or more anchoring features while maintaining a relatively small compressed size that allows for transcatheter delivery of the valve.

BRIEF SUMMARY OF THE INVENTION

The present invention is directed to an anchor hook system for a transcatheter heart valve replacement.

Accordingly, the present invention is directed to an anchoring system for a transcatheter prosthetic tricuspid or mitral heart valve, comprising:
an anchor hook having an elongated shaft portion and a hook portion at a distal end of the elongated shaft portion, a shaft tether loop on the shaft portion, and a tether mount on the hook portion,
a plurality of anchoring tabs or barbs disposed along the shaft portion,
a delivery catheter,
an anchor channel disposed within the valve,
an elongated pusher cable detachably attached to a proximal end of the shaft portion, and extending proximally through the delivery catheter,
an elongated tether attached to the tether mount and threaded through the shaft loop, and extending proximally through the delivery catheter,
the anchor hook made from shape memory material and the anchor hook heat-set into an open or expanded configuration where the hook portion extends away from a central axis of the shaft portion, and the anchor hook adjustable to a closed or compressed configuration by exerting a pulling force on the tether in a proximal direction where the hook portion is folds towards the shaft portion,
the anchoring tabs or barbs heat-set into an open or expanded configuration where the tabs or barbs extend away from the central axis of the shaft portion, and the tabs or barbs adjustable to a closed or compressed configuration by exerting a pulling force on the pusher cable in a proximal direction where the tabs or barbs are folded towards the shaft portion as the shaft portion is drawn into the delivery catheter, where the anchoring tabs or barbs in an expanded configuration have a radius from the central axis larger than an inner diameter of the anchor channel.

In another preferred embodiment, the anchoring system includes wherein the channel is integrated into or attached to an exterior surface of a valve body portion of the transcatheter prosthetic tricuspid or mitral heart valve.

In another preferred embodiment, the anchoring system includes wherein the channel is integrated into or attached to an interior surface of a valve body portion of the transcatheter prosthetic tricuspid or mitral heart valve.

In another preferred embodiment, the anchoring system includes wherein the shaft portion is selected from a single elongated member with the anchoring tabs or barbs extending away from the elongated member, or a chain of diamond-shaped cells with the anchoring tabs or barbs extending from lateral points of the diamond-shaped cells.

In another preferred embodiment, the anchoring system includes wherein the hook portion is selected from a single diamond-shaped cell, or a diamond-shaped cell with one or more anchoring tabs or barbs extending from lateral points of the diamond-shaped cell.

In another preferred embodiment, the anchoring system includes a second anchor hook attached to a second pusher cable and a second tether, said second cable and tether disposed within a second delivery catheter, said second catheter configured to be inserted thru a second anchor channel.

In another preferred embodiment, the anchoring system includes wherein the anchor hook is compressed within a cylindrical channel integrated into or attached to a valve body portion of the transcatheter prosthetic tricuspid or mitral heart valve, and wherein the cylindrical channel extends through the valve body vertically or at an angle up to 45 degrees from vertical, wherein vertical is parallel to a central atrial-to-ventricle axis of the transcatheter prosthetic tricuspid or mitral heart valve.

In another preferred embodiment, the anchoring system includes wherein the shaft has between 2-6 tabs or barbs, and wherein the channel is a cylinder of polyester or is cylinder lined with polyester.

In yet another preferred embodiment, the invention includes an orthogonally delivered (side-delivered) transcatheter prosthetic heart valve having an anchoring system, comprising:

the anchoring system;
a self-expanding annular support frame, the anchoring system mounted on or within the annular support frame, said annular support frame having a central channel and an outer perimeter wall circumscribing a central vertical axis in an expanded configuration, said annular support frame having a distal side and a proximal side,
a flow control component mounted within the annular support frame and configured to permit blood flow in a first direction through an inflow end of the valve and block blood flow in a second direction, opposite the first direction, through an outflow end of the valve,
wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis,
wherein the horizontal axis of the compressed configuration of the valve is substantially parallel to a lengthwise cylindrical axis of the delivery catheter,
wherein the valve has a height of about 5-60 mm and a diameter of about 25-80 mm.

In yet another preferred embodiment, the valve includes wherein the channel has a radio-opaque marker.

In yet another preferred embodiment, the valve includes wherein the channel is braided polyethylene, treated pericardial tissue, ePTFE, or Nitinol.

In yet another preferred embodiment, the valve includes wherein the tether or strap has a tooth-portion and a slidable locking element with a tooth-engaging pawl element.

In yet another preferred embodiment, the valve includes wherein the annular support frame further comprises a distal anchoring tab mounted on the distal side of the annular support frame, and a proximal anchoring tab mounted on the proximal side of the annular support frame.

In yet another preferred embodiment, the valve includes wherein the annular support frame is comprised of a plurality of compressible wire cells having an orientation and cell geometry substantially orthogonal to the central vertical axis to minimize wire cell strain when the annular support frame is configured in a vertical compressed configuration, a rolled compressed configuration, or a folded compressed configuration.

In yet another preferred embodiment, the valve includes wherein the annular support frame has a lower body portion and an upper collar portion, wherein the lower body portion in an expanded configuration forms a shape selected from a funnel, cylinder, flat cone, or circular hyperboloid.

In yet another preferred embodiment, the valve includes wherein said annular support frame is comprised of a braided, wire, or laser-cut wire frame, and said annular support frame is covered with a biocompatible material.

In yet another preferred embodiment, the valve includes wherein the annular support frame has a side profile of a flat cone shape having a diameter R of 40-80 mm, a diameter r of 20-60 mm, and a height of 5-60 mm.

In yet another preferred embodiment, the valve includes wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In yet another preferred embodiment, the valve includes wherein the annular support frame has a side profile of an hourglass shape having a top diameter R1 of 40-80 mm, a bottom diameter R2 of 50-70 mm, an internal diameter r of 20-60 mm, and a height of 5-60 mm.

In yet another preferred embodiment, the valve includes wherein the valve in an expanded configuration has a central vertical axis that is substantially parallel to the first direction.

In yet another preferred embodiment, the valve includes wherein the flow control component has an internal diameter of 20-60 mm and a height of 10-40 mm, and a plurality of leaflets of pericardial material joined to form a rounded cylinder at an inflow end and having a flat closable aperture at an outflow end.

In yet another preferred embodiment, the valve includes wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battens, rigid or semi-rigid panels, and combinations thereof.

In yet another preferred embodiment, the valve includes wherein the distal anchoring tab is comprised of wire loop, a wire frame, a laser cut frame, an integrated frame section, or a stent, and the distal anchoring tab extends from about 10-40 mm away from the distal side of the annular support frame.

In yet another preferred embodiment, the valve includes wherein the proximal anchoring tab is comprised of wire loop, a wire frame, a laser cut frame, an integrated frame section, or a stent, and the distal anchoring tab extends from about 10-40 mm away from the proximal side of the annular support frame.

In yet another preferred embodiment, the valve includes further comprising an upper distal anchoring tab attached to a distal upper edge of the annular support frame, the upper distal anchoring tab comprised of wire loop, a wire frame, a laser cut frame, an integrated frame section, or a stent, and extends from about 2-20 mm away from the annular support frame.

In yet another preferred embodiment, the valve includes wherein the outer perimeter wall comprises a front wall portion that is a first flat panel and a back wall portion that is a second flat panel, and wherein a proximal fold area and a distal fold area each comprise a sewn seam, a fabric panel, a rigid hinge, or a flexible fabric span without any wire cells.

In yet another preferred embodiment, the valve includes wherein the annular support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

In yet another preferred embodiment, the invention includes a method for deploying an anchor hook system for a prosthetic transcatheter heart valve, comprising:

(i) advancing a delivery catheter thru an anchor channel of a transcatheter heart valve to a subannular position, (ii) pushing an anchor hook out of a distal end of the delivery catheter using an elongated pusher cable that is disposed within the delivery catheter and attached to a proximal end of a shaft portion of the anchor hook, the shaft portion having anchoring tabs or barbs disposed along the shaft portion and a hook portion attached to a distal end of the shaft portion, wherein the hook portion and the anchoring tabs or barbs are initially compressed against the shaft portion when within the delivery catheter, and the hook portion and the anchoring tabs or barbs expand to a heat-set shape-memory open configuration when expelled from the delivery catheter, (iii) pulling the shaft portion of the anchor hook into the anchor channel by pulling the pusher cable in a proximal direction, wherein pulling the shaft portion retracts the hook portion in a proximal direction and captures native leaflet tissue or native chordae tendineae within or on the hook portion of the anchor hook, and the retracted hook portion presses the native leaflet tissue or native chordae tendinea against a subannular portion of the prosthetic transcatheter heart valve or a subannular surface of the native annulus, and wherein pulling the shaft portion of the anchor hook into the anchor channel draws the opened/expanded tabs/barbs into the anchor channel, where the anchor channel has a narrower cylindrical radius than the extended radius of the tabs/barbs and causes the tabs/barbs to partially fold toward the shaft portion, and create a tensioning force with the tabs/barbs pressing against an interior surface of the anchor channel, wherein the anchor channel is a mesh or braid and the tabs/barbs penetrate or grip the interior surface of the anchor channel.

In yet another preferred embodiment, the method of deploying includes wherein the native leaflet tissue is tricuspid leaflet tissue.

In yet another preferred embodiment, the method of deploying includes wherein the native leaflet tissue is mitral leaflet tissue.

In yet another preferred embodiment, the method of deploying includes wherein the native leaflet tissue is mitral leaflet tissue, and wherein the anchor hook system comprises, a first anchor hook with hook portion extended and then retracted to capture a P2 mitral leaflet, and a second anchor hook with hook portion extended and then retracted to capture a A2 mitral leaflet.

In yet another preferred embodiment, the method of deploying includes the step of retrieving the anchor hook, wherein the delivery catheter slides over the shaft portion while the tabs/barbs are engaging the anchor channel, and flattens the tabs/barbs back towards or against the shaft portion, thus disengaging the tabs/barbs from the anchor channel, wherein the delivery catheter is advanced distally to a subannular/ventricular position to release the hook portion from the captured native tissue, wherein a tether that is attached to the anchor hook is pulled and folds the hook portion against the shaft portion, wherein the entire anchor hook is then pulled into the delivery catheter, and wherein the delivery catheter is withdrawn and/or the anchor hook is redeployed.

In yet another preferred embodiment, the invention includes a process for manufacturing an anchoring hook for an orthogonally delivered (side-delivered) transcatheter prosthetic heart valve frame, comprising: using additive or subtractive metal or metal-alloy manufacturing to produce the anchoring hook, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining.

In yet another preferred embodiment, the invention includes a method of using the anchoring hook system for orthogonal delivery of implantable prosthetic heart valve to a desired location in the body, the method comprising the steps:

(i) advancing a delivery catheter to the desired location in the body and delivering an expandable prosthetic heart valve with an anchoring hook system to the desired location in the body by releasing the valve from the delivery catheter, and (ii) anchoring an anchoring hook attached to the valve into native tissue, wherein the valve comprises an annular support frame having a flow control component mounted within the annular support frame and configured to permit blood flow in a first direction through an inflow end of the valve and block blood flow in a second direction, opposite the first direction, through an outflow end of the valve, the anchoring hook system attached to the annular support frame, a distal anchoring tab mounted on a distal side of the annular support frame, and a proximal anchoring tab mounted on a proximal side of the annular support frame, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, and wherein the valve has a height of about 5-60 mm and a diameter of about 25-80 mm.

In yet another preferred embodiment, the method of using includes wherein releasing the valve from the delivery catheter is selected from the steps consisting of:

(i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In yet another preferred embodiment, the method of using includes wherein the step of anchoring an anchoring hook attached to the valve into native tissue, comprises the steps of expelling the anchoring hook from the channel, extending the hook portion of the anchoring hook, capturing native tissue, and pulling the tether to compress the anchoring hook.

In yet another preferred embodiment, the method of using includes the additional step of positioning the distal anchoring tab of the heart valve prosthesis into the right ventricular outflow tract of the right ventricle.

In yet another preferred embodiment, the method of using includes the additional steps of positioning the distal anchoring tab of the heart valve prosthesis into the right ventricular outflow tract of the right ventricle, and positioning an upper distal anchoring tab into a supra-annular position, and the upper distal anchoring tab providing a supra-annular downward force in the direction of the ventricle and distal anchoring tab providing a sub-annular upward force in the direction of the atrium.

In yet another preferred embodiment, the method of using includes the additional step of rotating the heart valve prosthesis using a steerable catheter along an axis parallel to the plane of the valve annulus.

In yet another preferred embodiment, the invention includes a method for orthogonal delivery of implantable prosthetic heart valve having the anchoring hook system in the body, the method comprising the steps:
  (i) advancing a distal end of a guide wire to a distal location, wherein the distal location is a pulmonary artery or a left ventricle of a heart, wherein the guide wire starts outside of a patient using femoral vein access or brachiocephalic vein access, and extends through an inferior vena cava or a superior vena cava to a right atrium, and extends from the right atrium through the tricuspid valve to the pulmonary artery or extends from the right atrium across the atrial septum in a transseptal access through the mitral valve and into a left ventricle;
  (ii) advancing a delivery catheter over the guide wire to a target location, where the target location is a right atrium of the tricuspid valve or a left atrium of the mitral valve;
  (iii) advancing and delivering an orthogonally compressed (compressed for side-delivery) self-expandable prosthetic heart valve to the target location in the body, wherein a compressed configuration of the valve has a long-axis substantially parallel to a length-wise cylindrical axis of the delivery catheter,
  wherein the expanded configuration of the valve has a height of about 5-60 mm and a diameter of about 25-80 mm,
  wherein the valve comprises an annular support frame having a flow control component mounted within the annular support frame and configured to permit blood flow in a first direction through an inflow end of the valve and block blood flow in a second direction, opposite the first direction, through an outflow end of the valve,
  a distal anchoring tab is mounted on a distal side of the annular support frame, the distal anchoring tab having a length of 10-40 mm and a width of 2-10 mm, wherein the guide wire is threaded through a threading aperture on or within the distal anchoring tab,
  at least one proximal anchoring tab is mounted on a proximal side of the annular support frame, the proximal anchoring tab having a length of 2-25 mm and a width of 2-10 mm, and
  a valve advancing tool comprising an elongated sheath wherein the guide wire is within a lumen of the sheath, wherein the outer diameter of the sheath is larger than the inner diameter of the threading aperture on the distal anchoring tab, wherein when the sheath is advanced over the guide wire in a distal direction, and a distal end of the sheath contacts a proximal surface of the threading aperture, the valve is advanced distally through the delivery catheter by the distally-directed pulling force that the sheath imparts to the distal anchoring tab;
  (iv) partially releasing the valve from the delivery catheter by advancing the sheath over the guide wire, and positioning the distal anchoring tab at a desired anchoring area of the target location,
  wherein the desired anchoring area is selected from a right ventricular outflow tract (RVOT) of a right ventricle, and a sub-annular area below an A1-P1 antero-lateral commissure of a mitral valve,
  wherein positioning the distal anchoring tab holds the valve at a raised angle of at least 30 degrees to a localized annular plane relative to the horizontal axis of the valve and the delivery catheter,
  wherein partially releasing the valve permits blood to flow partially around the prosthetic valve and through the native leaflets, and partially through the flow control component of the prosthetic valve to provide a gradual blood flow transition from flow through native leaflets to complete flow through the prosthetic valve;
  (v) completing release of the entire valve from the delivery catheter by advancing the sheath over the guide wire, seating the valve in the native annulus by applying a downward force in the direction of the ventricle;
  (vi) seating the at least one proximal anchoring tab at a second desired anchoring area; and
  (vii) capturing native tissue using the anchor hook.

In yet another preferred embodiment, the invention includes a method for improving hemodynamic flow during implantation of a transcatheter prosthetic heart valve, comprising:
  (i) advancing a delivery catheter to the desired location in the body and delivering the valve of claim 9 to the desired location in the body;
  (ii) partially releasing the valve from the delivery catheter to establish blood flow around the partially released valve and establish blood flow through the flow control component;
  (iii) completely releasing the valve from the delivery catheter while maintaining attachment to the valve with a positioning catheter or wire to transition to increased blood flow through the flow control component and decreasing blood flow around the valve; and
  (iv) deploying the valve into a final mounted position to transition to complete blood flow through the flow control component and minimal or no blood flow around the valve;
  (v) anchoring the valve using the anchor hook; and
  (vi) disconnecting and withdrawing the positioning catheter or wire from the valve.

In yet another preferred embodiment, the method for improving hemodynamic flow includes wherein the distal anchoring tab is an RVOT tab positioned in the RVOT during the transition from partial release of the valve to complete release of the valve.

BRIEF DESCRIPTION OF THE SEVERAL VIEWS OF DRAWING

Figure 20:
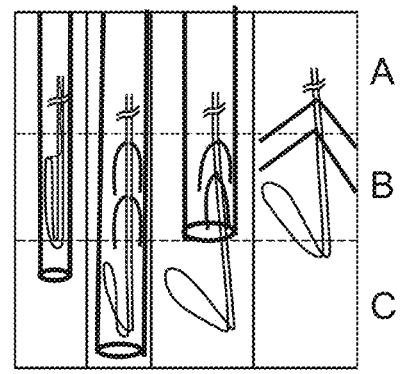

FIG. 20 is an illustration of a side view of a series (left to right) showing how an anchor hook can progress from (i) a stowed position within a delivery catheter sheath/channel, (ii) to an extended anchor position, (iii) to an extended open position, and (iv) to a retracted position, with an indicator of relative depths A-B-C referring to (A) above the annulus, (B) at or near the annular plane, and (C) below the annulus, according to the invention.

Figure 21:
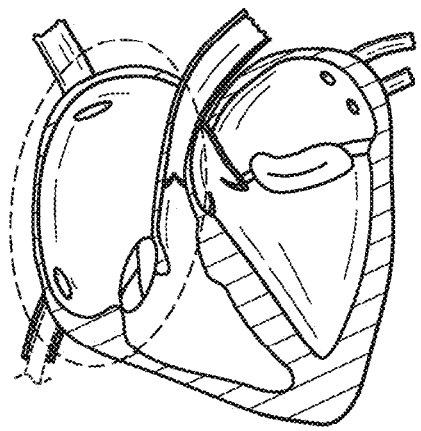

FIG. 21 is an illustration of a valve delivery process for an orthogonally delivered (side-delivered) valve, and shows a side view of a heart, with dashed circle showing a tricuspid region of interest.

Figure 22:
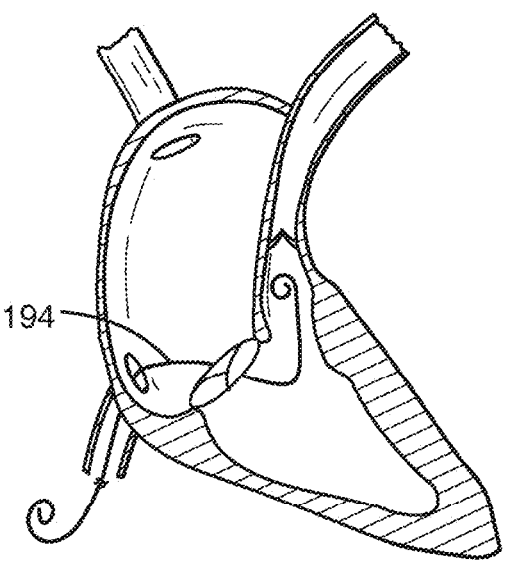

FIG. 22 is an illustration of a valve delivery process for an orthogonally delivered (side-delivered) valve, and shows a side view of a guide wire step of a multi-step delivery process.

Figure 23:
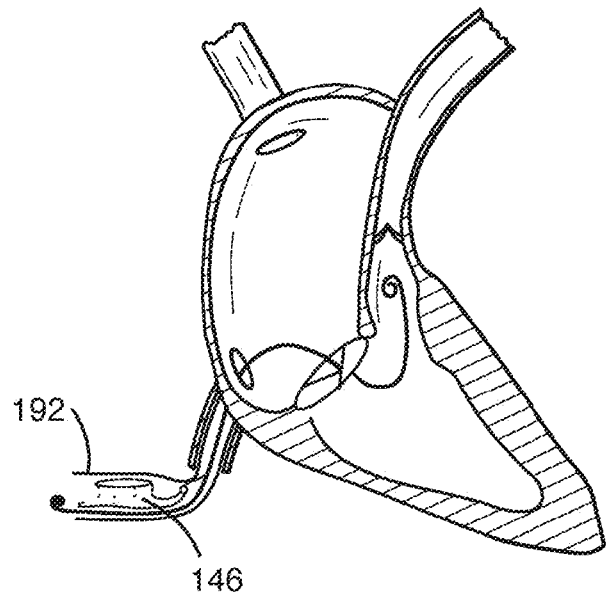

FIG. 23 is an illustration of a valve delivery process for an orthogonally delivered (side-delivered) valve, and shows a side view of a catheter delivery step of a multi-step delivery process, with a catheter containing an orthogonally compressed valve delivered via the IVC.

Figure 24:
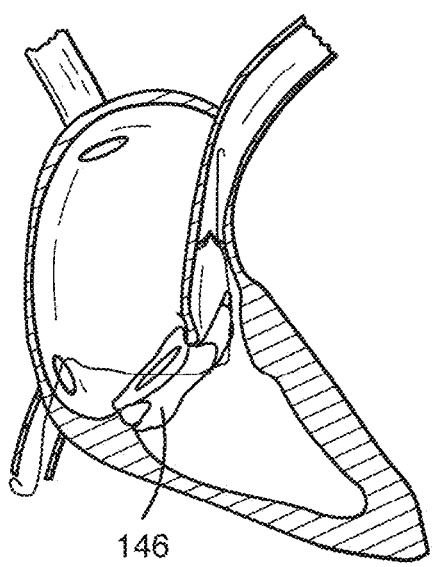

FIG. 24 is an illustration of a valve delivery process for an orthogonally delivered (side-delivered) valve, and shows a side view of a valve deployment step of a multi-step delivery process, with a catheter expelling an expanded uncompressed valve partially into the tricuspid annulus, with RVOT tab placed in the pulmonary artery right ventricular outflow tract (RVOT) anchoring area.

Figure 25:
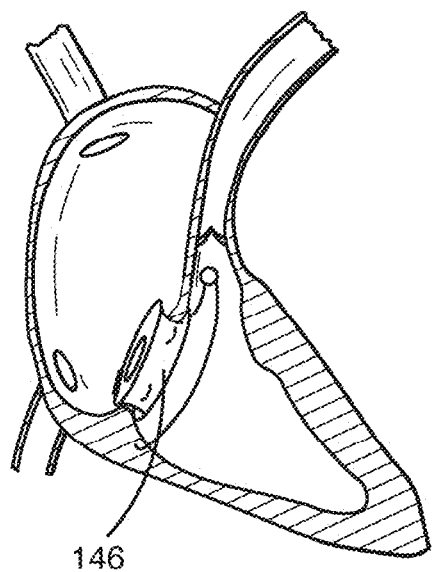

FIG. 25 is an illustration of a valve delivery process for an orthogonally delivered (side-delivered) valve, and shows a side view of a catheter delivery step of a multi-step delivery process, with a TVR valve fully seated within the tricuspid annulus, RVOT tab, and proximal tab positioned to secure the valve, and subannular anchor devices delivered and inserted into position on or in the valve.

Figure 26:
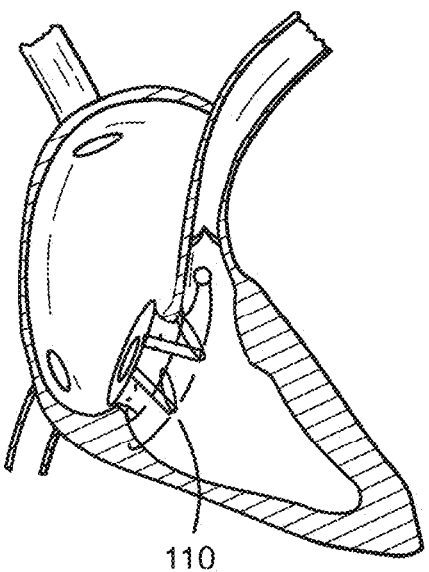

FIG. 26 is an illustration of an anchor hook delivery process, and shows a side view TVR valve fully seated within the tricuspid annulus, RVOT tab, and proximal tab positioned to secure the valve, and subannular anchor devices extended subannularly to capture native tissue, e.g. annular ring, chordae, and/or leaflet.

Figure 27:
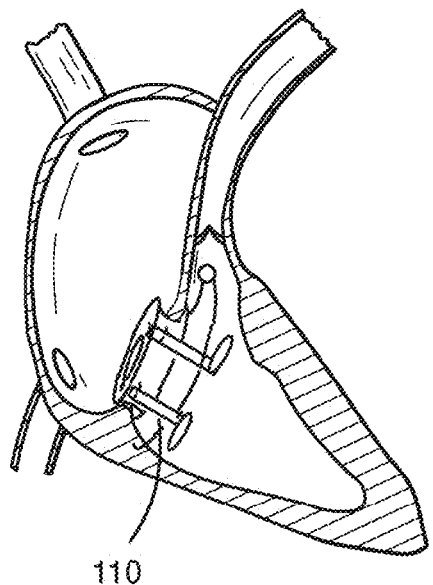

FIG. 27 is an illustration of an anchor hook delivery process, and shows a side view of a TVR valve fully seated within the tricuspid annulus, RVOT tab, and proximal tab positioned to secure the valve, and subannular anchor devices retracted after capture of native tissue, e.g. annular ring, chordae, and/or leaflet.

FIG. 28 is an illustration of side perspective view of the relation of the anchor hook(s) to native tissue during the anchoring-tissue capture process, with an indicator of relative depths A-B-C referring to (A) above the annulus.

FIG. 29 is an illustration of side perspective view of the relation of the anchor hook(s) to native tissue during the anchoring-tissue capture process, with an indicator of relative depths A-B-C referring to (B) at or near the annular plane.

FIG. 30 is an illustration of side perspective view of the relation of the anchor hook(s) to native tissue during the anchoring-tissue capture process, with an indicator of relative depths A-B-C referring to (C) below the annulus.

FIG. 31 is an illustration of an anchor hook that has been adjusted from a compressed configuration, to an extended/opened configuration to capture native tissue.

FIG. 32 is an illustration of an anchor hook that has been adjusted from an open position to a retracted, and/or cinched configuration.

Figure 33:
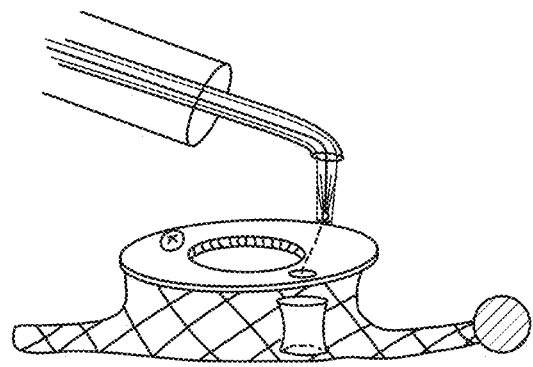

FIG. 33 is an illustration of a side perspective view of an anchor delivery catheter delivering an anchor hook to a radiomarker spot on the valve collar, according to the invention.

Figure 34:
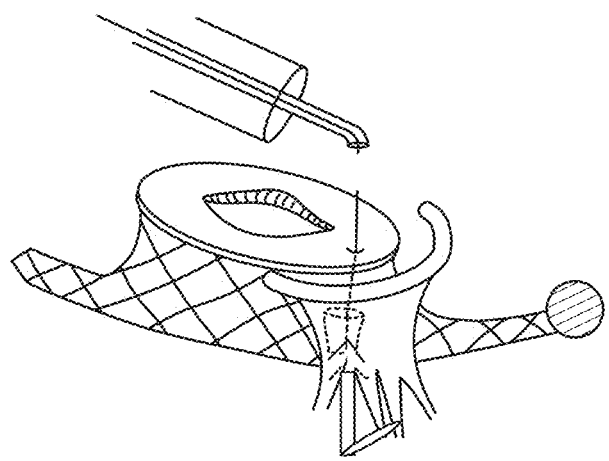

FIG. 34 is an illustration of a side perspective view of an anchor hook deployed to a sub-annular position, according to the invention.

Figure 35:
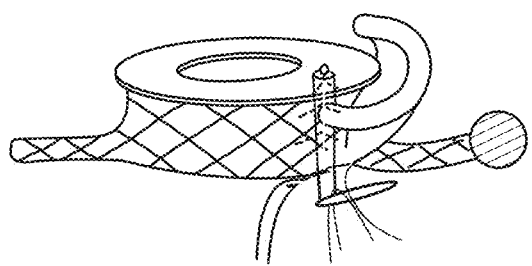

FIG. 35 is an illustration of a side perspective view of an anchor hook that has been deployed to a sub-annular position, and then retracted to capture the chordae and part of the anterior leaflet, according to the invention.

Figure 36:
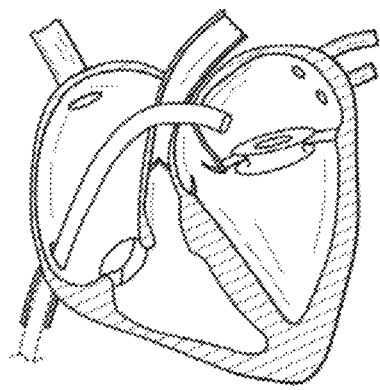

FIG. 36 is an illustration of a side perspective view a transcatheter delivery catheter that has access to the mitral valve from the IVC thru a trans-septal access to deliver an orthogonally deliverable (side-deliverable) mitral valve replacement prosthesis.

Figure 37:
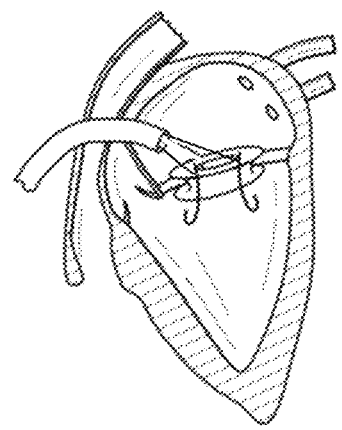

FIG. 37 is an illustration of a side perspective view a mitral valve embodiment having the anchor hooks deployed to an expanded position, according to the invention.

Figure 38:
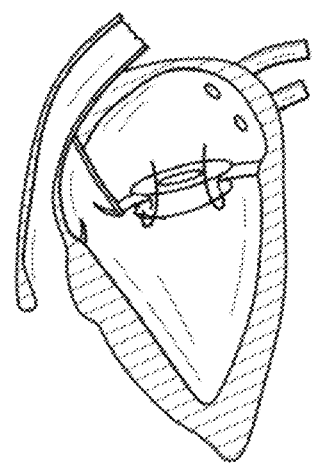

FIG. 38 is an illustration of a side perspective view a mitral valve embodiment having the anchor hooks compressed and/or cinched to capture native tissue, according to the invention.

Figure 39:
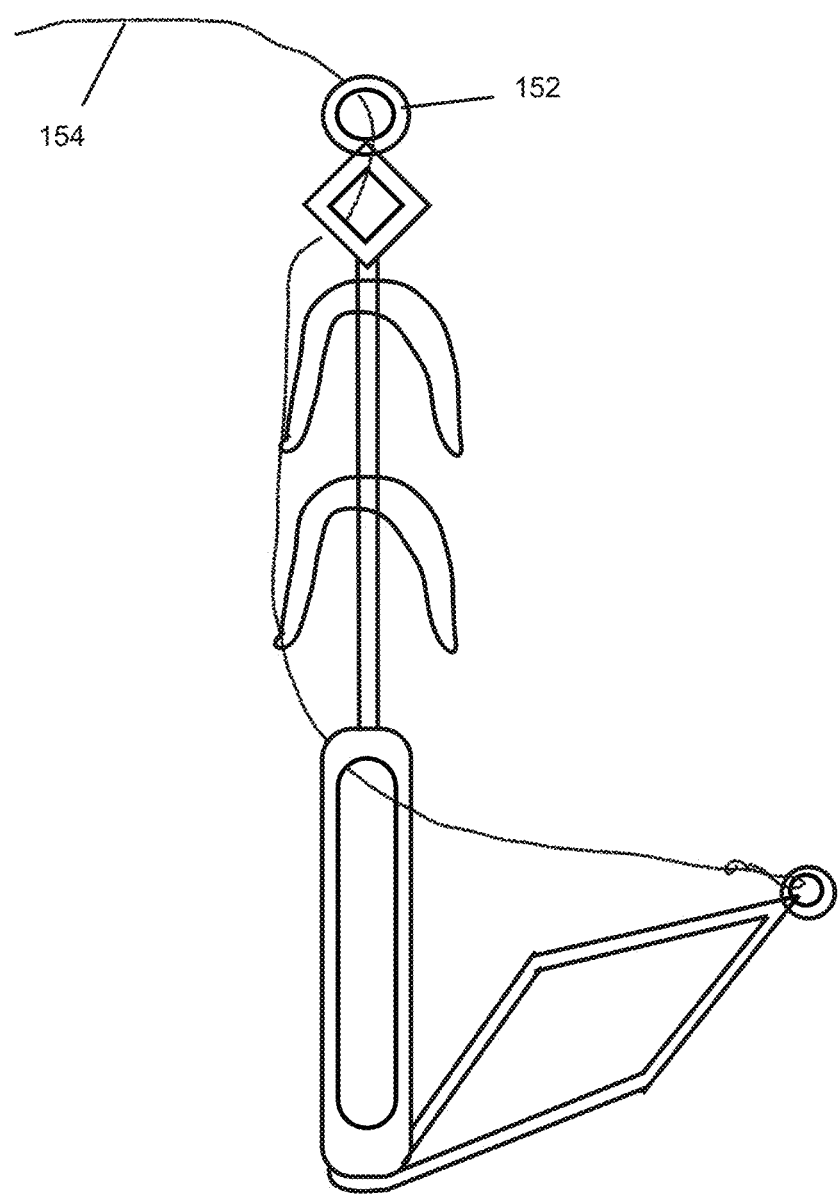

FIG. 39 is an illustration of one embodiment of an anchor hook according to the invention.

Figure 40:
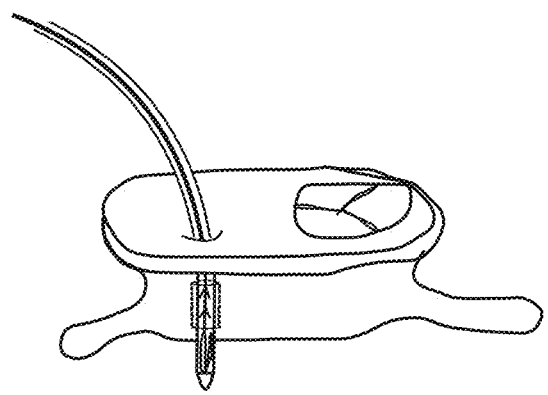

FIG. 40 is an illustration of one embodiment of an anchor hook disposed within a delivery catheter that extends through an anchor channel in the valve body to a subannular tissue-capture position, according to the invention.

Figure 41:
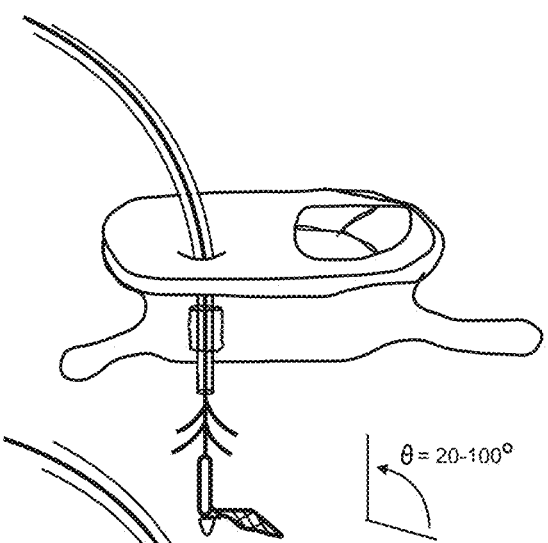

FIG. 41 is an illustration of one embodiment of an anchor hook released from the delivery catheter allowing the shape-memory material to expand with anchoring tabs or barbs extending laterally, and hook portion extending away from the shaft portion, according to the invention.

Figure 42:
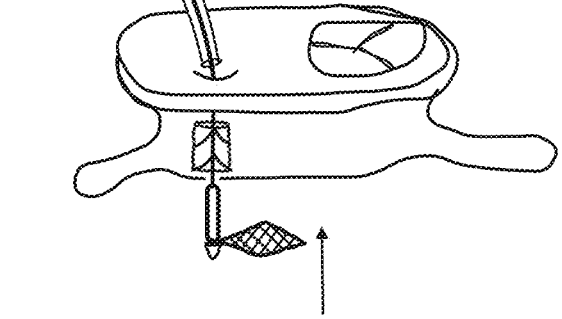

FIG. 42 is an illustration of one embodiment of an anchor hook partially pulled back into the anchor channel with anchoring tabs or barbs compressed into the lumen of the anchor channel, and lower shaft portion and hook portion remaining outside of the anchor channel for capture and securement/anchoring of native tissue to the valve body, according to the invention.

FIG. 43 is an illustration of a native mitral valve from a top perspective view above the annular plane from a trans-septal access side view, and shows the A2 leaflet and P2 leaflet in a partially open position.

FIG. 44 is an illustration of a native mitral valve from a bottom perspective view below the annular plane from a P2 side view, and shows the A2 leaflet and P2 leaflet in a partially open position.

FIG. 45 is an illustration of a native mitral valve from a bottom perspective view below the annular plane from an A2 side view, and shows the A2 leaflet and P2 leaflet in a partially open position.

FIG. 46 is an illustration of a prosthetic transcatheter heart valve from a plan or side view, and shows a pair of anchor hooks, each disposed within an anchor channel on the exterior surface of the valve body.

FIG. 47 is an illustration of a prosthetic transcatheter heart valve from a plan or side view, and shows a pair of anchor hooks, each disposed within an anchor channel within the cylinder of the valve body.

Figure 48:
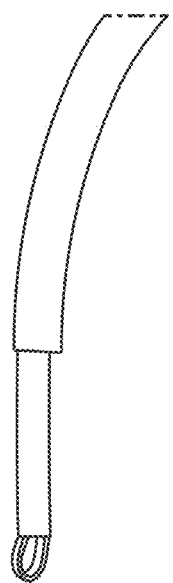

FIG. 48 is an illustration of an anchor in a stowed or compressed delivery position.

Figure 49:
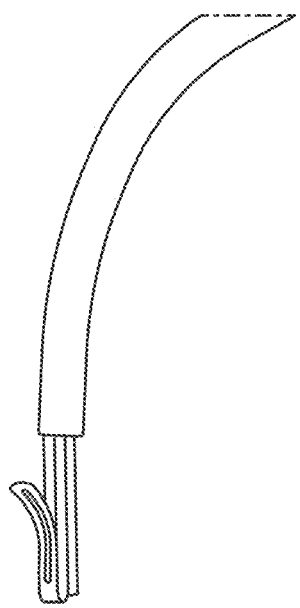

FIG. 49 is an illustration of an anchor in an expanded deployed position.

Figure 50:
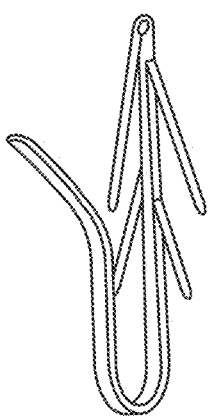

FIG. 50 is an illustration of an embodiment of a bare metal anchor element, according to the invention.

Figure 51:
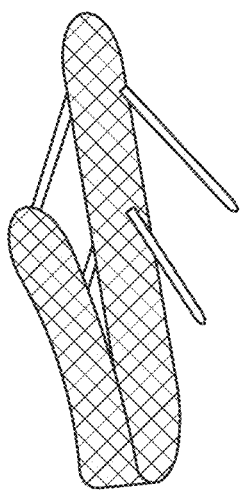

FIG. 51 is an illustration of an embodiment of an anchor element having a polyester cover along the shank of the anchor, according to the invention.

Figure 52:
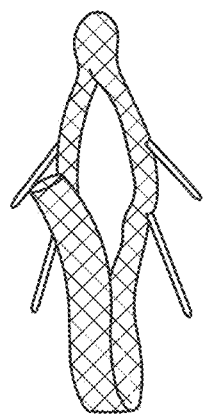

FIG. 52 is an illustration of an embodiment of a split shank anchor element having a polyester cover along the split shank of the anchor, according to the invention.

Figure 53:
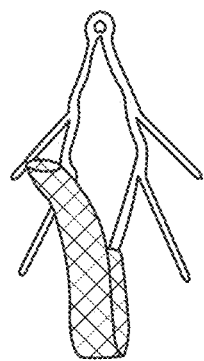

FIG. 53 is an illustration of an embodiment of a split shank anchor element having a bare metal split shank and a polyester cover on the bend or hook portion of the of the anchor, according to the invention.

Figure 54:
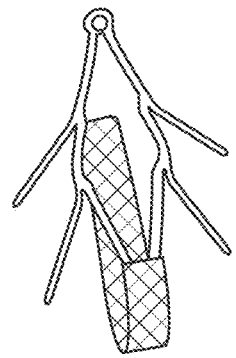

FIG. 54 is an illustration of an embodiment of a split shank anchor element having a bare metal split shank and a polyester cover on the bend or hook portion of the of the anchor, according to the invention.

Figure 55:
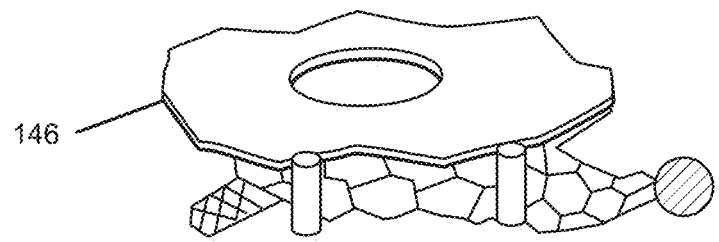

FIG. 55 is an illustration of a side perspective view of an orthogonally deliverable transcatheter heart valve with external anchor channel(s) positioned on the exterior of the valve, and extending from cuff/collar along the outer side surface of the valve body to the subannular/lower side, with distal right ventricular outflow tract (RVOT) tab, and proximal tab also shown, according to the invention.

Figure 56:
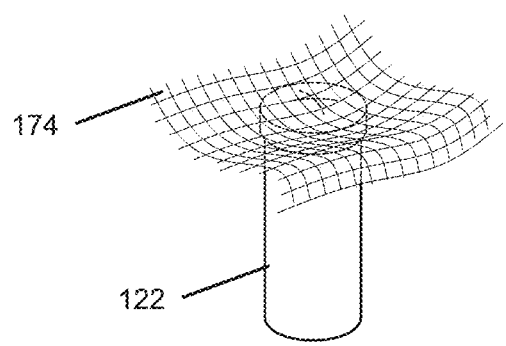

FIG. 56 is an illustration of a side perspective view of a channel having a mesh or tissue channel cover.

Figure 57:
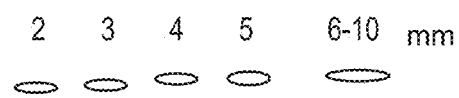

FIG. 57 is an illustration of varying diameter sizes of the channel(s).

Figure 58:
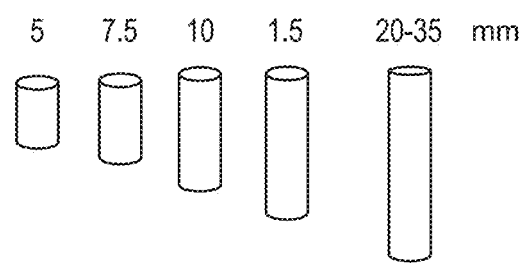

FIG. 58 is an illustration of varying channel length(s) of the channel(s).

Figure 59:

FIG. 59 is an illustration of a side perspective view of an embodiment of a channel and shows braided polyethylene as material for the channel.

Figure 60:
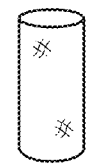

FIG. 60 is an illustration of a side perspective view of an embodiment of a channel and shows tissue as material for the channel.

Figure 61:

FIG. 61 is an illustration of a side perspective view of an embodiment of a channel and shows expanded polytetrafluoroethylene (ePTFE), as material for the channel.

Figure 62:

FIG. 62 is an illustration of a side perspective view of an embodiment of a channel and shows Nitinol® tube or stent, as material for the channel.

Figure 63:
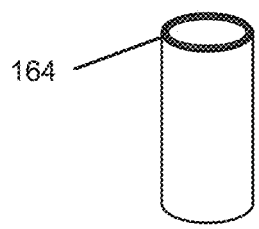

FIG. 63 is an illustration of radio-opaque marker locations on a channel, and specifically a top ring location.

Figure 64:
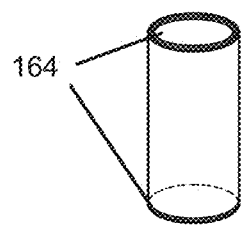

FIG. 64 is an illustration of radio-opaque marker locations on a channel, and specifically top and bottom ring locations.

Figure 65:
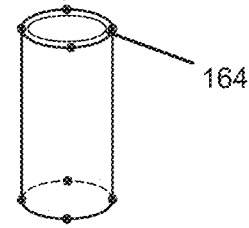

FIG. 65 is an illustration of radio-opaque marker locations on a channel, and specifically top and bottom alignment dot locations.

Figure 66:
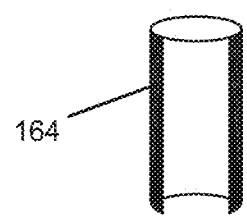

FIG. 66 is an illustration of radio-opaque marker locations on a channel, and specifically a side strip(s) location.

Figure 67:
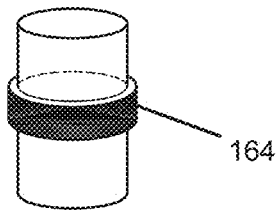

FIG. 67 is an illustration of radio-opaque marker locations on a channel, and specifically a mid-band location.

Figure 68:
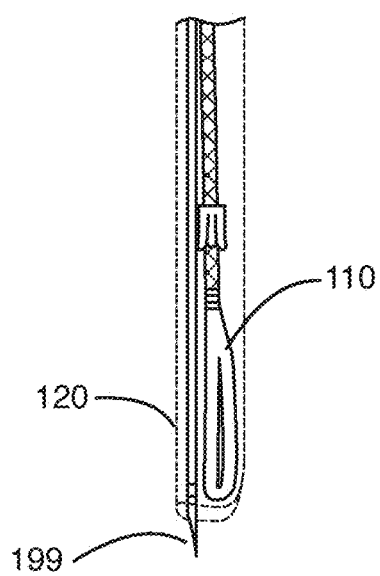

FIG. 68 is an illustration of a side view of a channel-less anchor deployment system with a tunneling catheter having a guide rod, a compressed tether lock, a compressed subannular anchor, disposed in a compressed configuration within the catheter, according to the invention.

Figure 69:
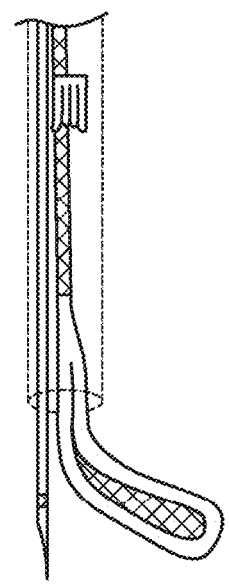

FIG. 69 is an illustration of a side view of a channel-less anchor deployment system with a tunneling catheter having a guide rod, a compressed tether lock, a partially expelled, partially uncompressed subannular anchor, according to the invention.

Figure 70:
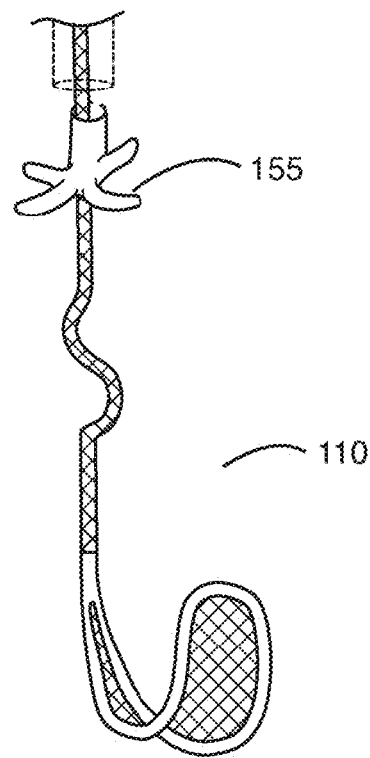

FIG. 70 is an illustration of a side view of a channel-less anchor deployment system with a tunneling catheter having an uncompressed expanded tether lock, and an uncompressed subannular anchor, according to the invention.

Figure 71:
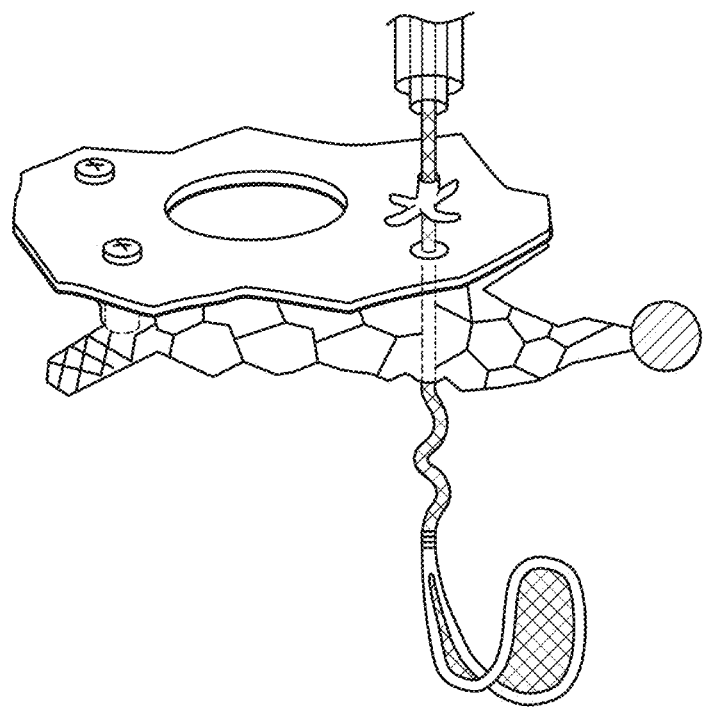

FIG. 71 is an illustration of a side perspective view of an orthogonally deliverable transcatheter heart valve with channel-less pre-determined anchor pathway(s) extending from cuff/collar through the valve body to the subannular/lower side, and distal right ventricular outflow tract (RVOT) tab, a proximal tab according to the invention according to the invention, with anchor delivery catheter, having subannular anchor connected by flexible tether to expandable tether lock, prior to cinching the lock down onto the collar surface and the tab against a lower portion of the valve body.

Figure 72:
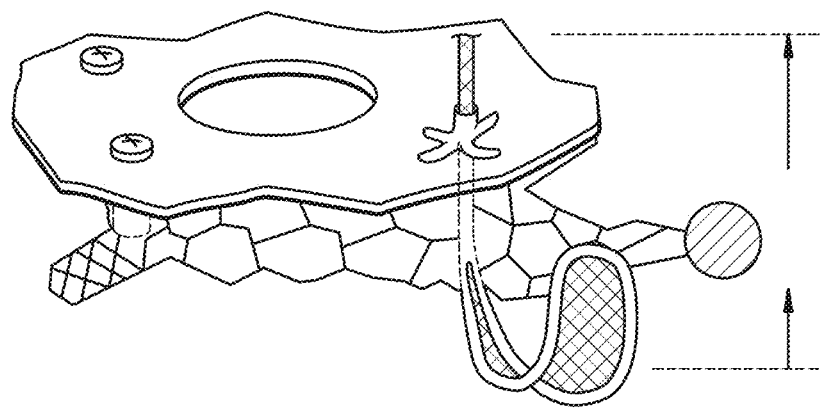

FIG. 72 is an illustration of a side perspective view of an orthogonally deliverable transcatheter heart valve with channel-less pre-determined anchor pathway(s) extending from cuff/collar through the valve body to the subannular/lower side, and distal right ventricular outflow tract (RVOT) tab, a proximal tab according to the invention according to the invention, with anchor delivery catheter, having subannular anchor connected by flexible tether to expandable tether lock, after cinching the lock down onto the collar surface and the tab against a lower portion of the valve body.

Figure 73:
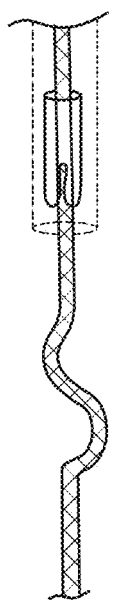

FIG. 73 is an illustration of a side view of a tether lock that is compressed within a delivery sheath (catheter), with the tether lock having a central aperture, with the braided tether threaded thru the central aperture of the tether lock so that the tether lock can slide along the tether.

Figure 74:
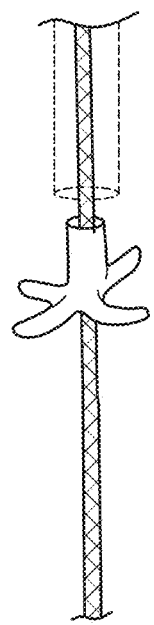

FIG. 74 is an illustration of a side view of a tether lock that is released by withdrawal of the sheath into an expanded, uncompressed configuration, with the expanded tether lock having a central aperture, and with the braided tether threaded thru the central aperture of the tether lock, and the central aperture having one or more locking teeth to tighten onto the tether and prevent further sliding along the tether. The locking teeth can be a curved, one-way type of pawl or tooth, or they may be piercing teeth that engage the tether when the tether lock is expanded.

Figure 75:
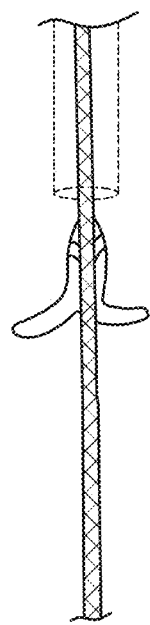

FIG. 75 is an illustration of a cross-sectional side view of a tether lock that is released by withdrawal of the sheath into an expanded, uncompressed configuration, with the expanded tether lock having a central aperture, and the central aperture having one or more locking teeth to tighten onto the tether and prevent further sliding along the tether. The locking teeth can be a curved, one-way type of pawl or tooth, or they may be piercing teeth that engage the tether when the tether lock is expanded.

Figure 76:
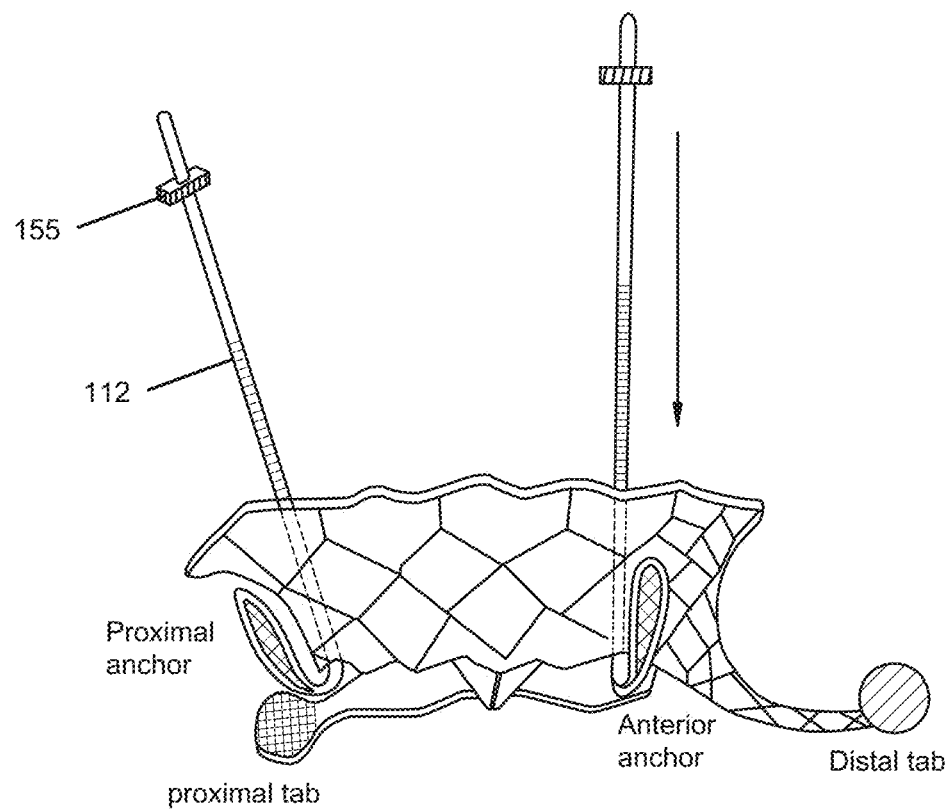

FIG. 76 is an illustration of another preferred embodiment of the invention and shows a compressible valve having a P anchor (near posterior leaflet) and an A anchor (near anterior leaflet), with the tissue anchor loops attached to flexible elongated straps or rods similar to a cable tie, the flexible elongated strap having an attached anchor lock that engages with a section of the strap having teeth, the anchor lock forming an encircling head with a pawl in the head that engages the teeth of the strap, such that when the anchor lock/head slides down the flexible elongated strap, the anchor lock/head is locked into place when the pawl prevents the anchor lock from sliding up the strap.

Figure 77:
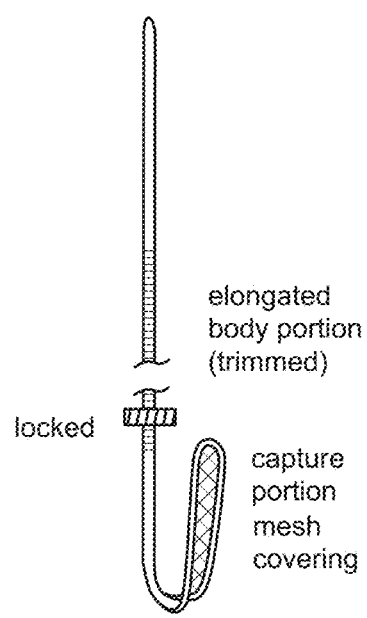

FIG. 77 is an illustration of a side view of a tissue anchor loop attached to a strap with anchor lock slid into a lower, locked position.

Figure 78:
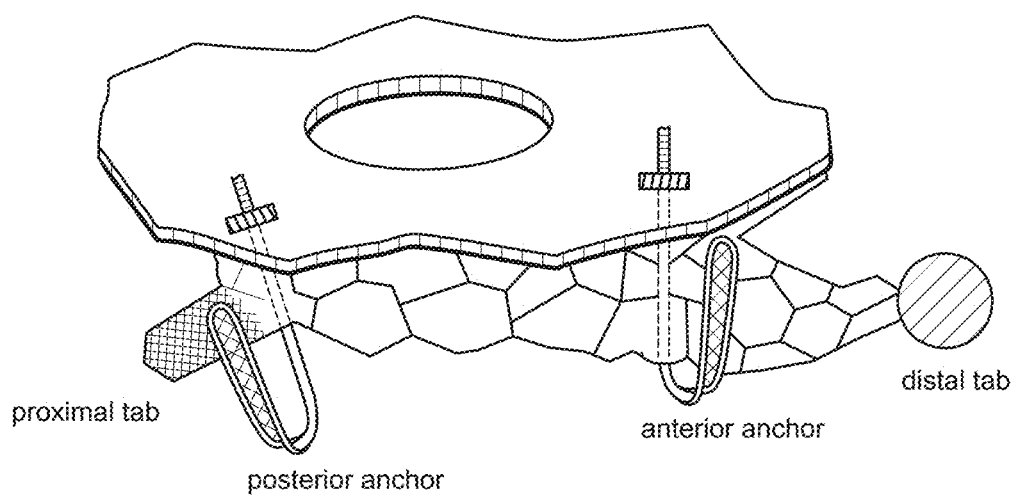

FIG. 78 is an illustration of a side perspective view towards a septal leaflet side of a tricuspid valve replacement with an upper collar attached to a body portion, with an RVOT tab, a proximal tab, a P anchor and an A anchor, with anchor locks slid down into a lower locking position.

Figure 79:
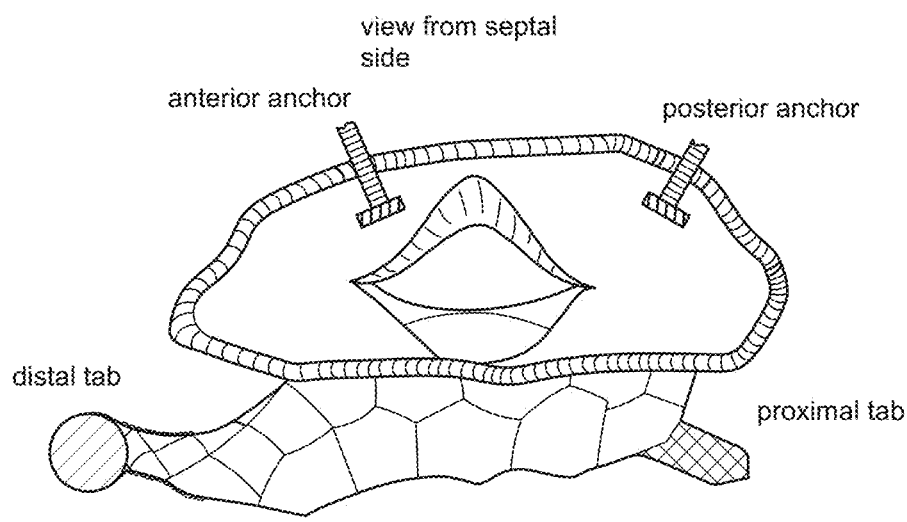

FIG. 79 is an illustration of a side perspective view from a septal leaflet side of a tricuspid valve replacement with an upper collar attached to a body portion, with an RVOT tab, a proximal tab, a P anchor and an A anchor, with anchor locks slid down into a lower locking position.

Figure 80:
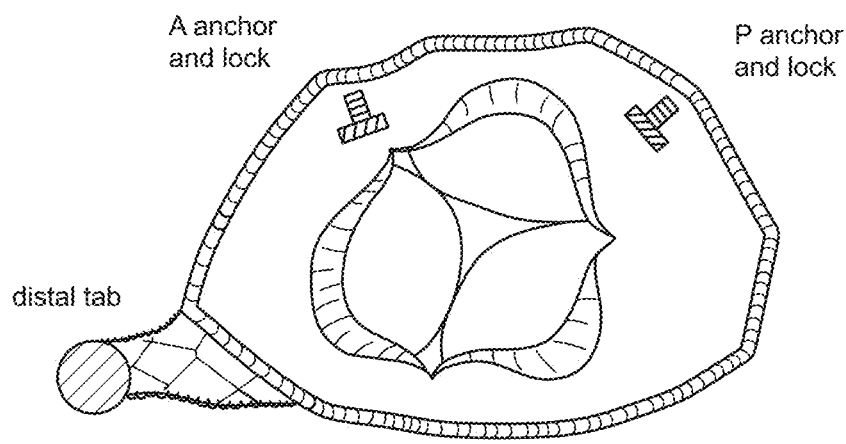

FIG. 80 is an illustration of a top view of a tricuspid valve replacement with an upper collar attached to a body portion, with an RVOT tab, a proximal tab, a P anchor and an A anchor, with anchor locks slid down into a lower locking position.

Figure 81:
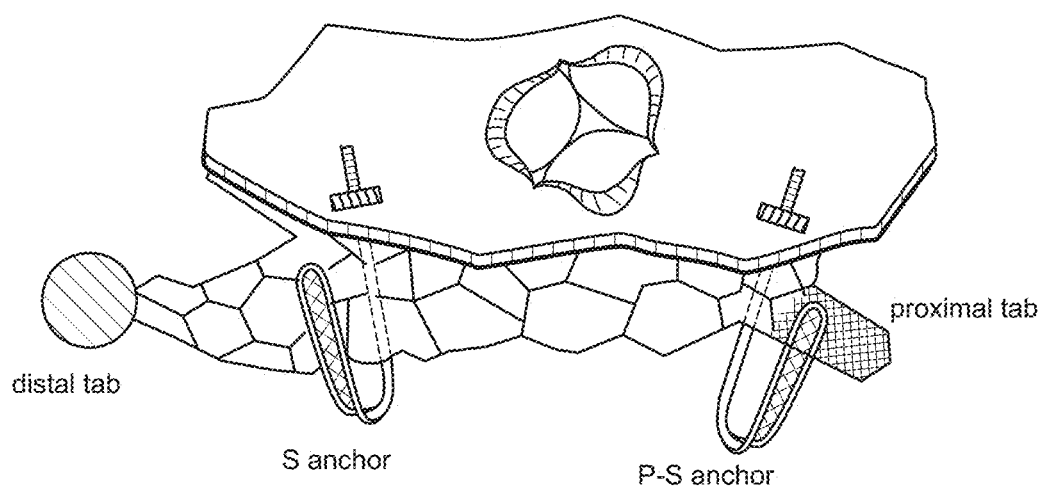

FIG. 81 is an illustration of a side perspective view from above a septal leaflet side of a tricuspid valve replacement with an upper collar attached to a body portion, with an RVOT tab, a proximal tab, central flow control element (tri-leaflet valve), an S anchor (anchor near septal leaflet) and a P-S anchor (anchor near postero-septal leaflet commissure), with anchor locks slid down into a lower locking position.

Figure 82:
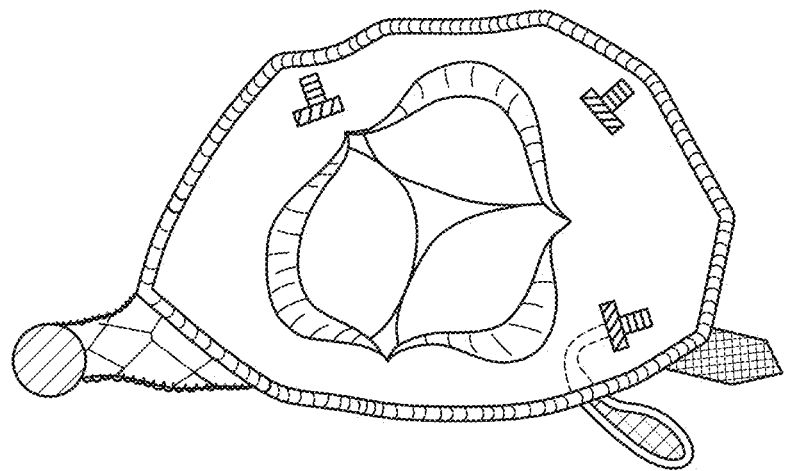

FIG. 82 is an illustration of a top view of a three-anchor tricuspid valve replacement with an upper collar attached to a body portion, with an RVOT tab, a proximal tab, central flow control element (tri-leaflet valve), an S anchor (anchor near septal leaflet), a P anchor (anchor near posterior leaflet), and an A anchor (near anterior leaflet), with anchor locks slid down into a lower locking position.

Figure 83:
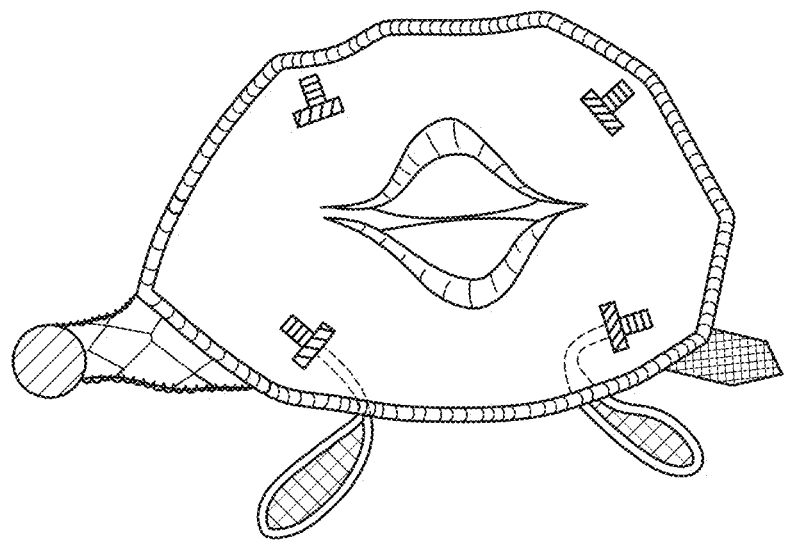

FIG. 83 is an illustration of a top view of a four-anchor tricuspid valve replacement with an upper collar attached to a body portion, with an RVOT tab, a proximal tab, central flow control element (tri-leaflet valve), an S anchor, a P anchor, a P-S anchor, and an A anchor, with anchor locks slid down into a lower locking position.

Figure 84:
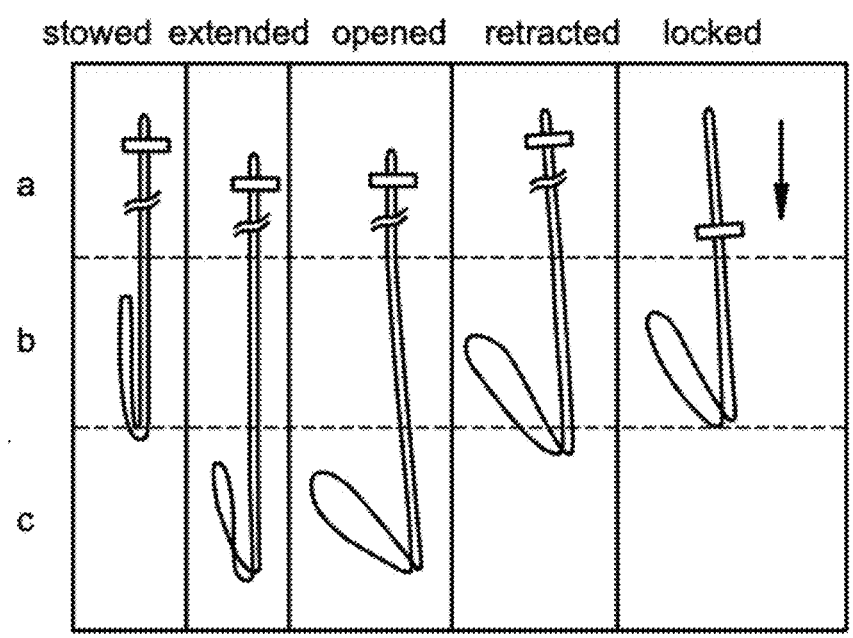

FIG. 84 is an illustration of a side view of a series showing how an anchor can progress from (i) a stowed position within a delivery catheter sheath, (ii) an extended anchor position, (iii) an extended open position, (iv) a retracted position, and (v) a locked position, with an indicator of relative depths A-B-C referring to (A) above the annulus, (B) at or near the annular plane, and (C) below the annulus, according to the invention.

FIGS. 85A-85F is an illustration of side perspective view of the relation of the anchor(s) to native tissue during the anchoring-tissue capture process, with an indicator of relative depths A-B-C referring to (A) above the annulus, (B) at or near the annular plane, and (C) below the annulus, with anchor configurations including (a) compressed shown in FIG. 85A, (b) extended shown in FIG. 85B, (c) opened shown in FIG. 85C, (d) retracted shown in FIG. 85D, (e) locked shown in FIG. 85E, and (f) trimmed shown in FIG. 85F, according to the invention.

Figure 86:
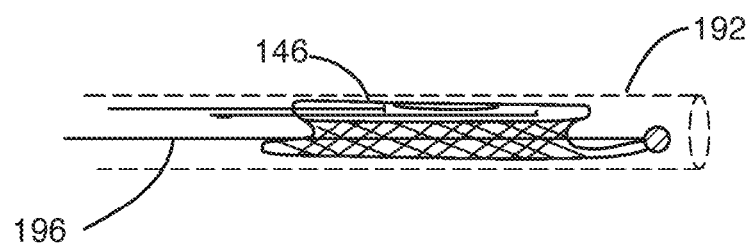

FIG. 86 is an illustration of a side view of an orthogonally compressed valve within a valve delivery catheter, with pre-attached folded over elongated straps and anchor locks and with advancement (towing) wire attached to the RVOT tab to pull the valve out of the sheath by applying force to the distal end, according to the invention.

Figure 87:
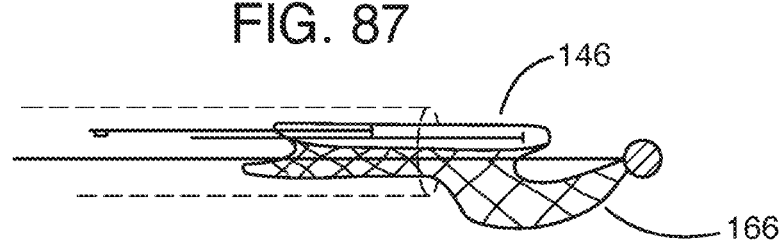

FIG. 87 is an illustration of a side view of a valve partially expelled from the delivery catheter by the advancement (towing) wire, with pre-attached folded over elongated straps and anchor locks, according to the invention.

Figure 88:
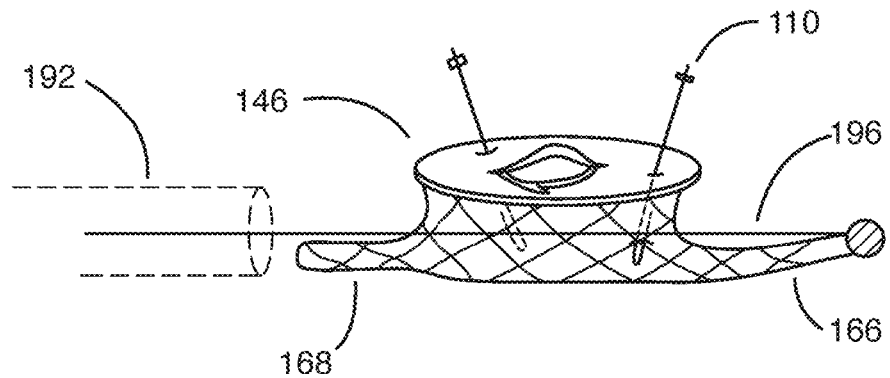

FIG. 88 is an illustration of a side view of a fully released valve, with pre-attached elongated straps and anchor locks released from the catheter sheath and in ready position for anchor deployment and tissue capture, according to the invention.

Figure 89:
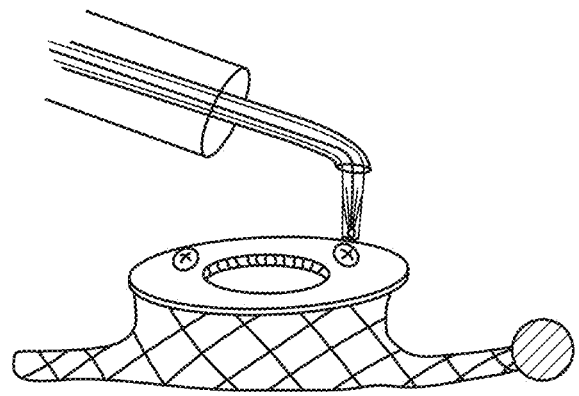

FIG. 89 is an illustration of a side perspective view of an anchor delivery catheter delivering an anchor to a radio-marker spot on the valve collar, according to the invention.

Figure 90:
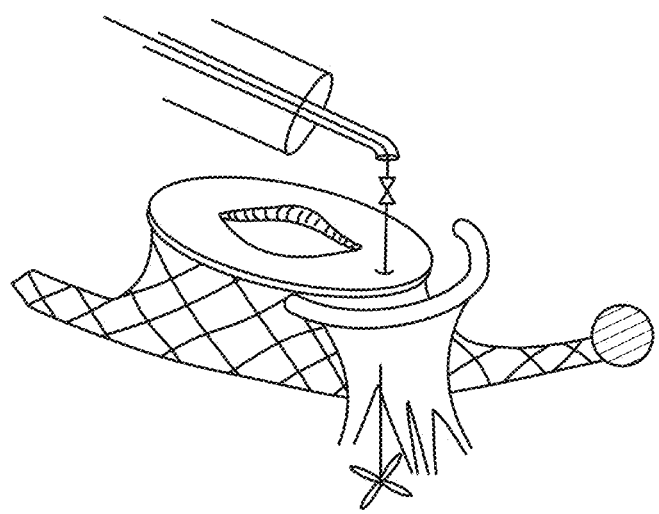

FIG. 90 is an illustration of a side perspective view of an anchor deployed to a sub-annular position, and a tether lock mounted on the tether above the valve collar ready for the tissue cinching step, according to the invention.

Figure 91:
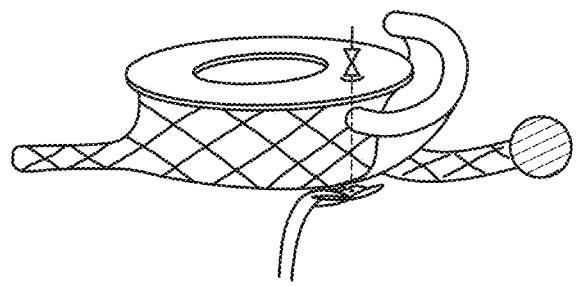
Figure 92A:
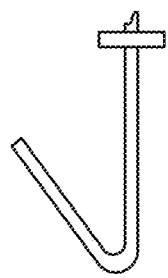
Figure 92B:
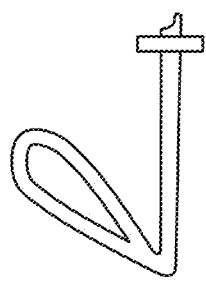
Figure 92C:
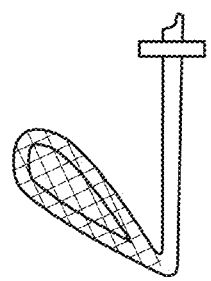
Figure 92D:
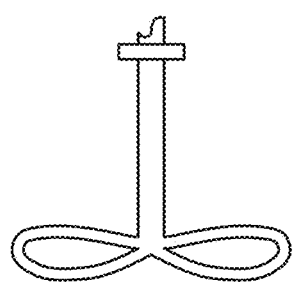
Figure 92E:
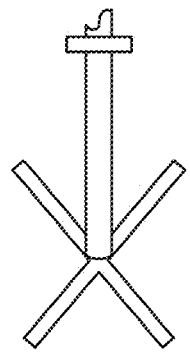
Figure 92F:
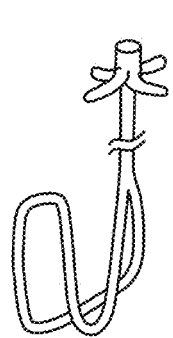
Figure 92G:
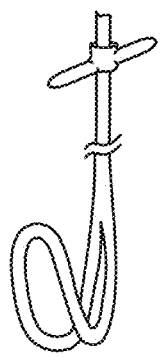

FIG. 91 is an illustration of a side perspective view of an anchor deployed to a sub-annular position, retracted to capture the chordae and part of the anterior leaflet, with the tether lock slid down the tether to the valve collar to lock the anchor and cinch the native tissue, according to the invention.

FIGS. 92A-92G are illustrations of a variety of anchor loops and tissue capture structures, according to the present invention.

DETAILED DESCRIPTION OF THE INVENTION

The invention is directed to anchor channels and subannular anchors for a dual-tab transcatheter heart valve replacement that is a low profile, orthogonally delivered (side-delivered) implantable prosthetic heart valve having an ring-shaped or annular support frame, an inner 2- or 3-panel sleeve, an elongated sub-annular distal anchoring tab extending into the right ventricular outflow tract, an elongated sub-annular proximal anchoring tab extending into the proximal sub-annular space, preferably between the anterior and the posterior leaflets.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Integrated Anchor Channel

In the description and claims herein, the term "integrated anchor channel", "channel", "anchor delivery channel", or "anchor delivery conduit" is used to describe a cylindrical tube or similar tubular structure that is from 5-35 mm in length having a diameter of 2-10 mm that is attached to (exterior) or extends through (interior) the body and/or collar portion of the prosthetic valve. The channel has, in some embodiments, at least one radio-opaque marker or radio-opaque material or structure so that the location of the channel can be visualized with a suitable imaging modality (i.e. a modality under which the radio-opaque marker or material is easily differentiated from other components of the prosthetic valve and surrounding tissue) and an anchor delivery system catheter can be guided through the body of a patient to the site where the valve is mounted or to be mounted and specifically to the location of the channel. In one embodiment, delivery of an orthogonal valve is (lengthwise delivery, height- and width-compression) through the femoral vein to the inferior vena cava (IVC) to the right atrium of the heart for anchoring the prosthetic tricuspid heart valve replacement, followed by IVC delivery of the anchoring system to install the sub annular anchors.

Orthogonal

In the description and claims herein, the term "orthogonal" is used to describe that the valves of the present invention are compressed and side-delivered at a roughly 90 degree angle compared to traditional iris-opening transcatheter heart valves. Traditional valves are iris-ing and have a central cylinder axis that is parallel to the length-wise axis of the delivery catheter and are deployed from the end of the delivery catheter in a manner akin to pushing a closed umbrella out of a sleeve. The valves of the present invention are compressed and delivered in a sideways manner. Traditional iris-ing valves can only be expanded as large as what the internal diameter of the delivery catheter will allow. Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the lengthwise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, e.g. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In some embodiments of the invention, the transcatheter approach includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-septal approach, e.g. fossa ovalis or lower, via the IVC-femoral or the SVC jugular approach.

Annular Support Frame

In the description and claims herein, the term "annular support frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In some embodiments, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular support frame has a flow control component mounted within the annular support frame and configured to permit blood flow in a first direction through an inflow end of the valve and block blood flow in a second direction, opposite the first direction, through an outflow end of the valve.

Since the frame is preferably made of superelastic metal or alloy such as Nitinol, the frame is compressible. Preferably, the frame is constructed of a plurality of compressible wire cells having an orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame may be about 5-60 mm in height, may have an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In some embodiments, the annular support frame used in the prosthetic heart valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating."

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers

The tethers are made from surgical-grade materials such as biocompatible polymer suture material. Non-limiting examples of such material include ultra-high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Tube and/or Cover Material—Biological Tissue

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic heart valve for implantation, and U.S. Pat. No. 5,336,616 to LifeCell Corporation discloses acellular collagen-based tissue matrix for transplantation.

Polymers

In one embodiment, the conduit may optionally be made from a synthetic material such a polyurethane or polytetrafluoroethylene. Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.l.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying Zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug Novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of embodiments of the reciprocating pressure conduit valve include the following details and features.

EXAMPLE

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In some embodiments the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that require balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example—Manufacturing Process

In some embodiments the invention includes a process for manufacturing an orthogonally delivered (side-delivered) transcatheter prosthetic heart valve frame, comprising:
(i) using additive or subtractive metal or metal-alloy manufacturing to produce a self-expanding annular support frame,
  wherein the additive metal or metal-alloy manufacturing is 3D printing or direct metal laser sintering (powder melt), and
  wherein the subtractive metal or metal-alloy manufacturing is photolithography, laser sintering/cutting, CNC machining, electrical discharge machining.

In other embodiments, there is provided a process for manufacturing an orthogonally delivered (side-delivered) transcatheter prosthetic heart valve frame, further comprising the steps of:
(ii) mounting a flow control component within the valve frame, said flow control component configured to permit blood flow along the central vertical axis through an inflow end of the flow control component and block blood flow through an outflow end of the valve, and
(iii) covering an outer surface of the valve frame with a pericardium material or similar biocompatible material.

Example—Compression Methods

In other embodiments, there is provided a method of compressing, wherein the implantable prosthetic heart valve is rolled or folded into a compressed configuration using a step selected from the group consisting of:
(i) unilaterally rolling into a compressed configuration from one side of the annular support frame;
(ii) bilaterally rolling into a compressed configuration from two opposing sides of the annular support frame;
(iii) flattening the annular support frame into two parallel panels that are substantially parallel to the long-axis, and then rolling the flattened annular support frame into a compressed configuration; and
(iv) flattening the annular support frame along a vertical axis to reduce a vertical dimension of the valve from top to bottom.

PARTS LIST 101 anchoring system
110 anchor hook
112 shaft portion
114 hook portion
116 cable mount
118 anchoring tabs or barbs
120 delivery catheter
122 anchor channel
124 elongated pusher cable
126 hook open configuration
128 hook closed configuration
130 radius of hook gap
132 barb open configuration
134 barb closed configuration
136 radius from shaft
138 inner diameter of channel
140 split shaft
142 second anchor hook
144 second anchor channel
146 side-delivered prosthetic transcatheter heart valve
148 lumen of anchor channel
150 tether mount on anchor hook portion
152 tether loop on shaft
154 tether
155 tether lock
156 valve body portion/outer perimeter wall
158 interior of valve body portion
160 exterior of valve body portion
162 polyester cylinder channel or polyester lining of channel
164 radio-opaque marker
166 distal tab
168 proximal tab
170 compressible wire cells of annular support frame
172 valve collar portion
174 biocompatible cover material
176 flow control component
178 leaflets
180 supports or ribs holding leaflets
182 upper anchoring tab
184 front wall
186 back wall
188 proximal fold area
190 distal fold area 192 delivery catheter for valve
194 guide wire
196 valve advancing tool/guide wire sheath
198 threading aperture on distal tab
199 piercing tool

DRAWINGS

Figure 1:
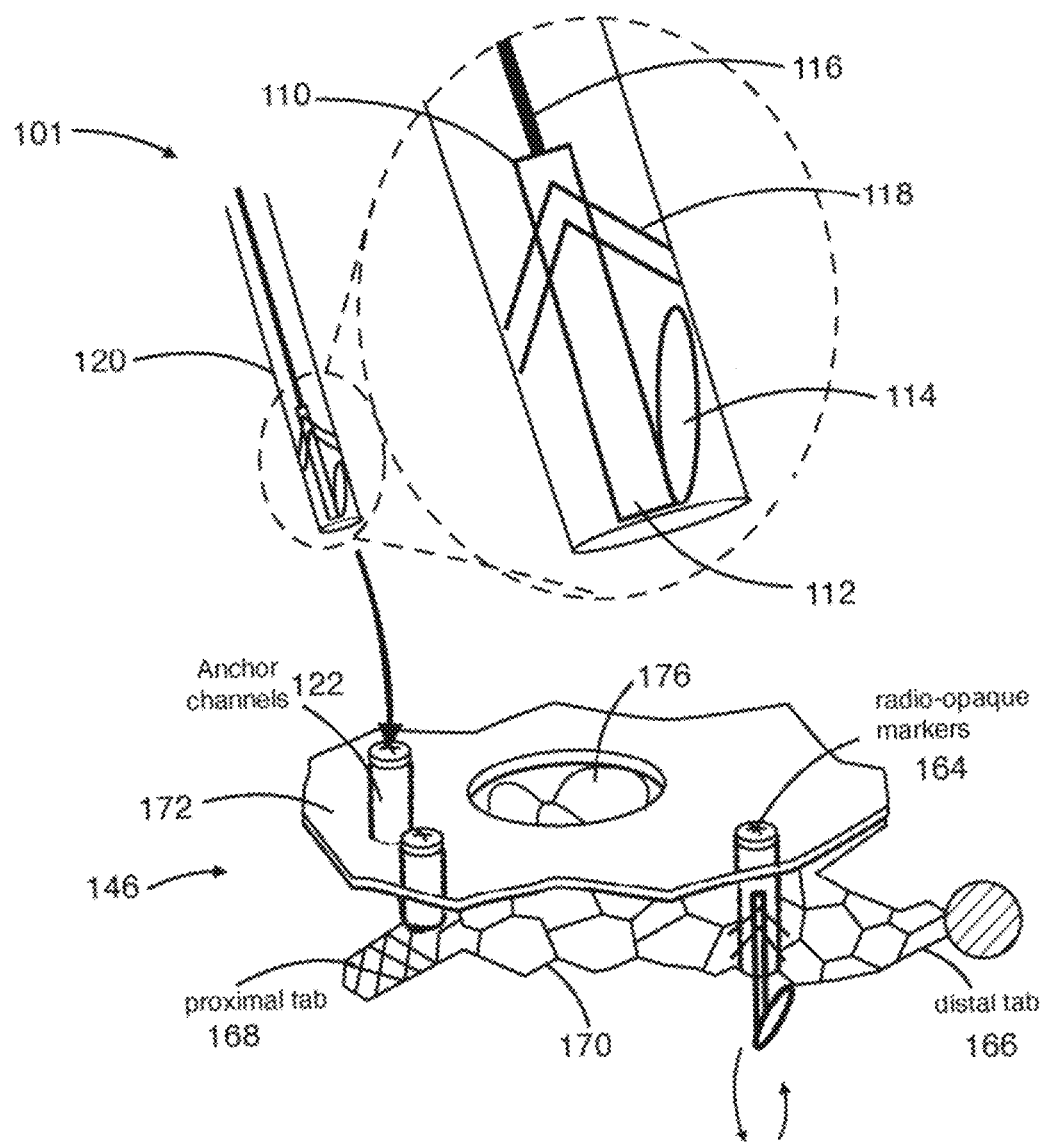
FIG. 1 is an illustration of an anchor hook according to the invention.

Referring now to the drawings, FIG. 1 is an illustration of an anchor hook 110 according to the invention. FIG. 1 shows an anchor hook 110 disposed within the lumen of a delivery catheter 120 for delivery thru a selected location on the valve collar 172 for subannular actuation and deployment. FIG. 1 includes a detail illustration of the anchor hook 110 of FIG. 1 and shows the collapsible/expandable anchor hook with downward hooking tabs or barbs 118 on the shaft portion 112 and shows the hook portion 114. In some embodiments, a tether 116 connects a tether mount on the hook portion to loop guide on the shaft portion for actuating the anchor hook from an open position to a closed position. FIG. 1 also shows an anchor hook 110 embodiment that is already mounted within an integral delivery conduit/channel 122 configured within the valve body 146. FIG. 1 also shows an orthogonally deliverable (side-deliverable) transcatheter heart valve 146 with integrated anchor conduit or channel(s) 122 extending from cuff/collar 172 through the valve body to the subannular/lower side, and distal right ventricular outflow tract (RVOT) tab 166, and a proximal tab 168, according to the invention.

Figure 2:
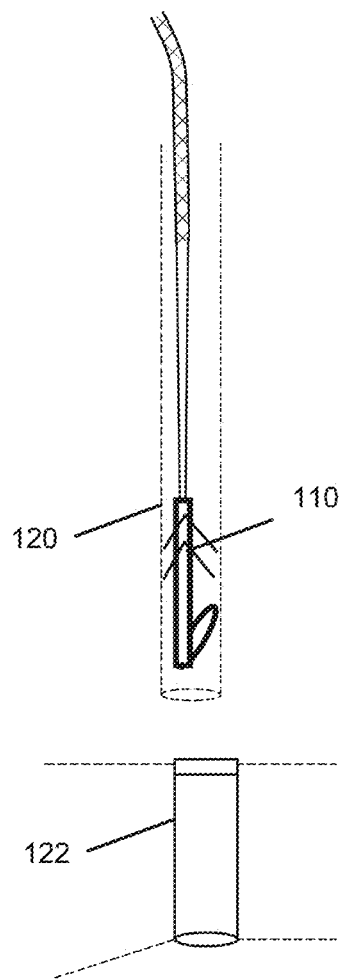
FIG. 2 is an illustration of a side view of an anchor delivery system according to the invention.

FIG. 2 is an illustration of a side view of an anchor delivery system according to the invention having a delivery catheter 120 sheathed over a compressed expandable anchor hook 110 attached to a pusher rod detachably connected to the anchor hook 110 for inserting into the channel 122.

FIGS. 3-6 shows a process of (i) extending the anchor hook 110 to a subannular position, (ii) releasing the anchor hook 110 from a compressed configuration to an open, expanded configuration, and capturing subannular tissue such as chordae tendinea and/or leaflet and/or annular tissue, with the unfolded, opened anchor hook 114, optionally re-compressing or re-folding the anchor hook, with the tissue captured in the hook portion 114 and/or the hooking tabs, and/or optionally cinching the anchor hook and captured tissue upwards against the bottom subannular surface of the valve body, and (iii) releasing the barbs 132 extending from the shank by withdrawing the sheath 120, allowing the barbs 132 to lodge in or thru the cylindrical inner wall of the anchor channel 122.

Figure 3:
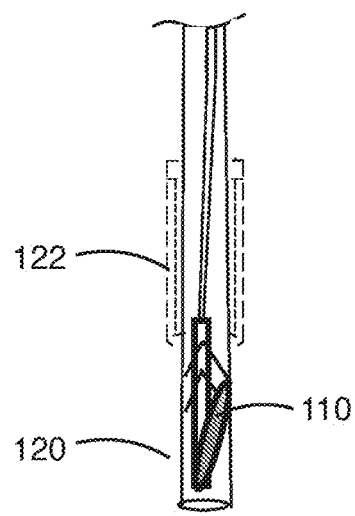
FIGS. 3-6 are illustrations of a step of a multi-part series showing a side view of a process of using an anchor hook from a delivery catheter.

FIG. 3 is an illustration of a step of a multi-part series showing a side view of a process of using an anchor hook 110 from a delivery catheter 120, with the anchor hook disposed within the delivery catheter, and the delivery catheter inserted thru the integrated anchor channel 122 in the valve, and with delivery catheter sheath at position 1.

Figure 4:
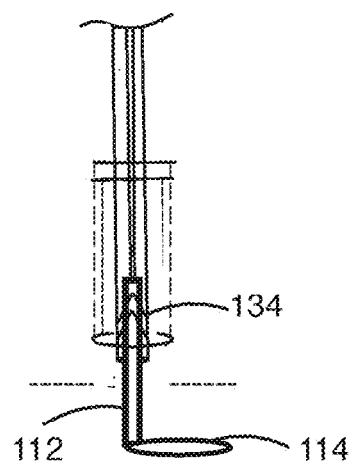

FIG. 4 is an illustration of a step of a multi-part series showing a side view of a process of using an anchor hook from a delivery catheter, with the anchor hook partially disposed within the lumen of the delivery catheter, and partially expelled out of the lumen by partial removal of the delivery catheter sheath to position 2.

Figure 5:
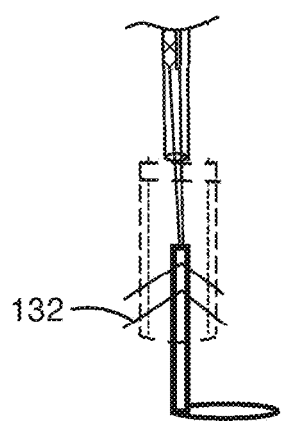

FIG. 5 is an illustration of a step of a multi-part series showing a side view of a process of using an anchor hook from a delivery catheter, with the bend portion 114 of the anchor hook expelled from the lumen by partial removal of the delivery catheter sheath to position 2, and with the anchor hook being adjusted/elongated to capture and secure native tissue or structures.

Figure 6:
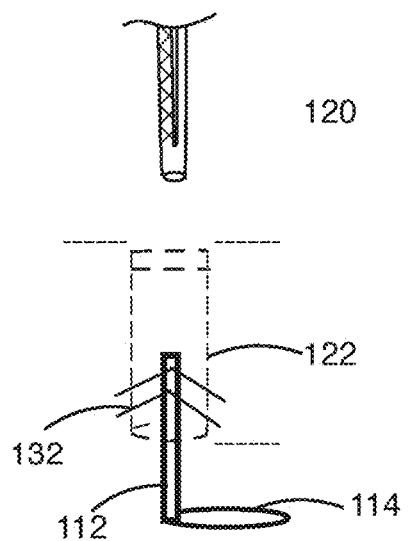

FIG. 6 is an illustration of a step of a multi-part series showing a side view of a process of using an anchor hook from a delivery catheter, with the anchor hook completely expelled from the lumen of the delivery catheter by withdrawal of the delivery catheter sheath to position 3, and compression and capture of the native tissue by adjusting or shortening the tether to close the anchor hook to a compressed configuration.

Figure 7:
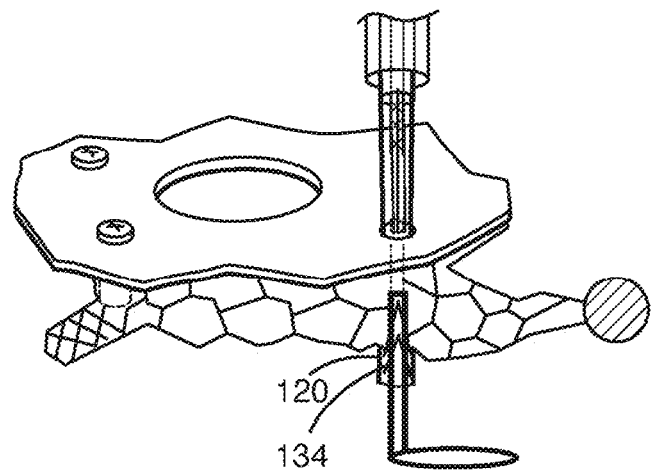
FIG. 7 is an illustration of a step of a series showing a side view of a process of expelling an anchor hook to a subannular position using a delivery catheter.

FIG. 7 is an illustration of a step of a series showing a side view of a process of expelling an anchor hook to a subannular position using a delivery catheter. Barbs 134 are in a compressed position.

Figure 8:
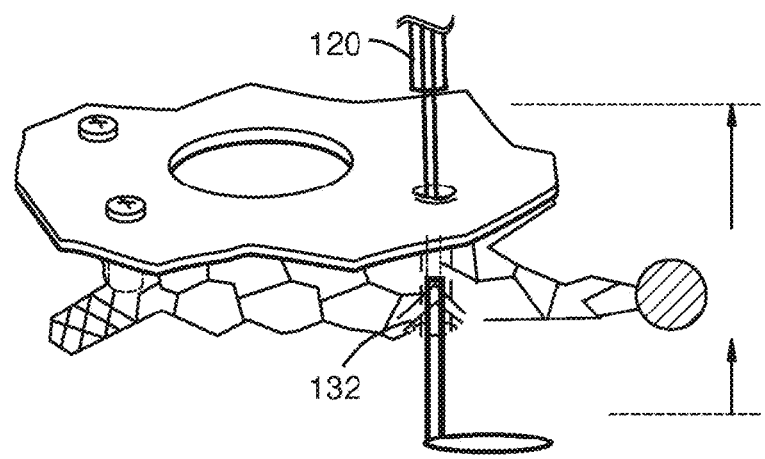
FIG. 8 is an illustration of a step of a series showing a side view of a process of capturing native tissue by pulling the tether to re-fold the hook portion against the shaft portion.

FIG. 8 is an illustration of a step of a series showing a side view of a process of capturing native tissue by pulling the hook portion, and cinching subannular tissue/structures against the bottom edge of the valve body/channel, while unsheathing the previous compressed/flattened and now opened barbs 132 to lock the anchor hook in place by lodging into the mesh channel, with the anchor hook spanning the channel, and tightened to a tensioned configuration along the cinch axis.

FIGS. 9-15 is a series of illustrations of another embodiment of the invention that uses a slidable lock 155 and tether instead of the expandable barbs to cinch and secure the anchor hook after the anchor hook has captured tissue.

Figure 9:
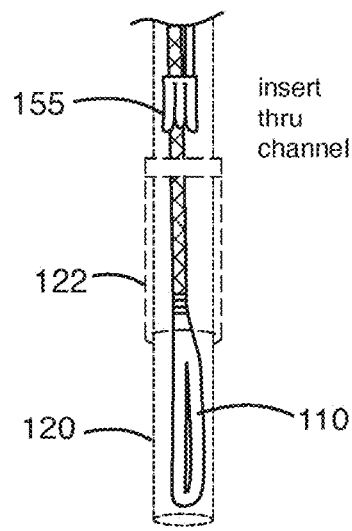
FIGS. 9-15 are an illustration of a step of a series showing a side view of a process of capturing native tissue by pulling the tether to re-fold the hook portion against the shaft portion.

FIG. 9 shows inserting the sheathed anchor hook 110 through the channel 122 to a subannular location.

Figure 10:
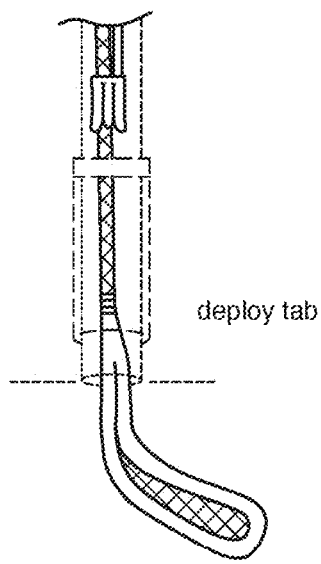

FIG. 10 shows the sheath 120 partially withdrawn to expel the hook or bend portion to capture native tissue.

Figure 11:
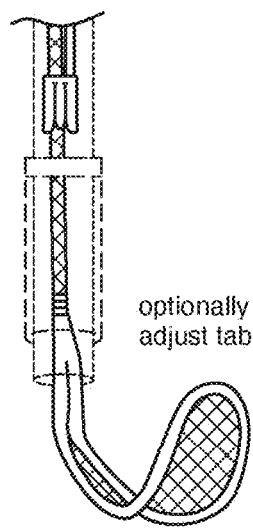

FIG. 11 show an optional step of adjusting or rotating the bend or hook portion.

Figure 12:
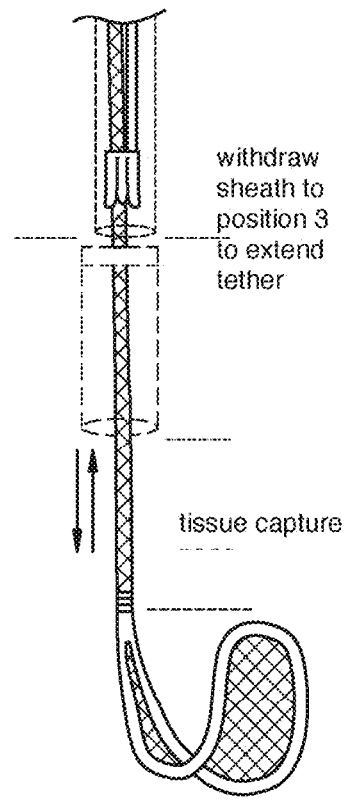

FIG. 12 shows the sheath withdrawn to an atrial position while the hook portion is located in a subannular or ventricular position.

Figure 13:
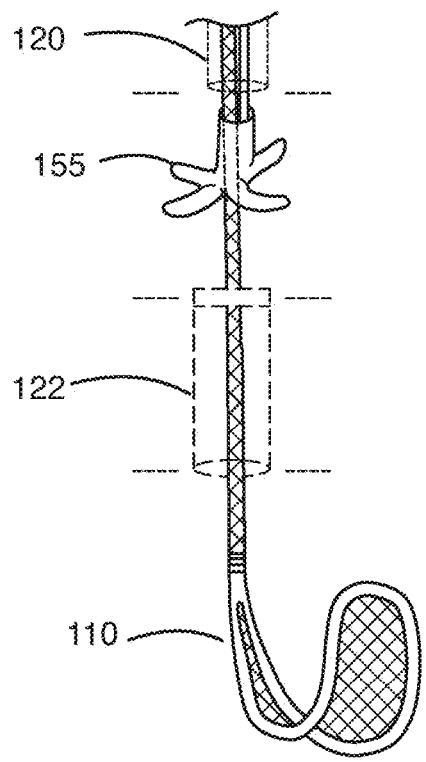

FIG. 13 shows the deployment of an expandable tether lock 155 that is expelled from the sheath 120 allowing it to expand to a size larger than the inner diameter of the channel 122.

Figure 14:
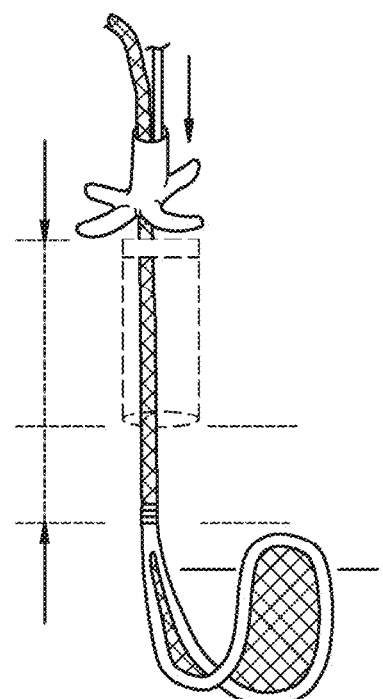

FIG. 14 shows the tether pulling the hook portion and native tissue up into a capture position while pushing the tether lock down onto the top of the upper part of the channel.

Figure 15:
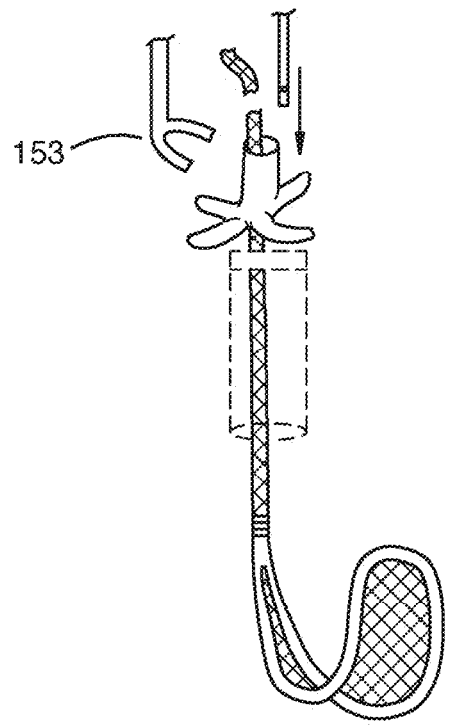

FIG. 15 shows the tether being trimmed 153 to leave the cinched anchor hook in the prosthetic valve.

Figure 16:
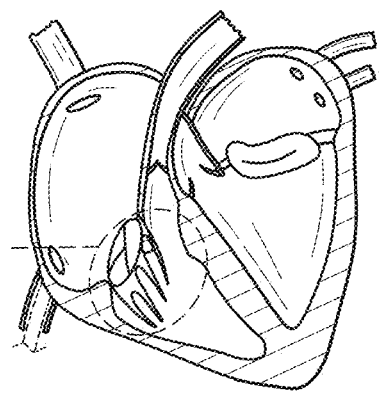
FIG. 16 is an illustration of a side view of a heart.

FIG. 16 is an illustration of a bisected view of a heart.

Figure 17:
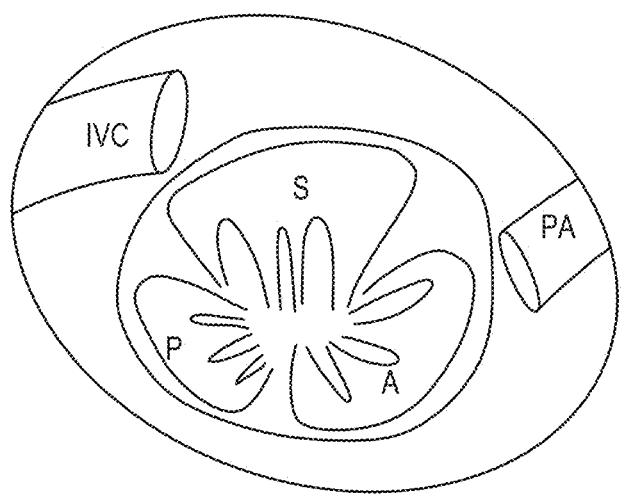
FIG. 17 is an illustration of a top view of a native tricuspid valve with location of inferior vena cava, location of pulmonary artery, and locations of the septal, posterior, and anterior leaflets.

FIG. 17 is an illustration of a top view of a native tricuspid valve with location of inferior vena cava, location of pulmonary artery, and locations of the septal, posterior, and anterior leaflets.

Figure 18:
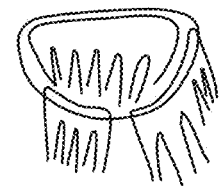
FIG. 18 is an illustration of a side perspective view of a tricuspid leaflets in isolation.

FIG. 18 is an illustration of a side perspective view of a tricuspid leaflets in isolation.

Figure 19:
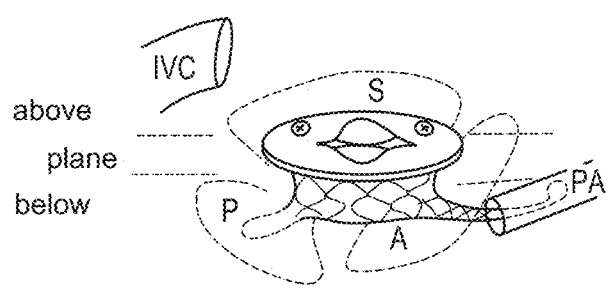
FIG. 19 is an illustration of an orthogonal transcatheter valve replacement (TVR) valve against illustrations of the location of native tissue, with IVC, PA, and the septal, posterior, and anterior leaflets, with an indicator of relative depths A-B-C referring to (A) above the annulus, (B) at or near the annular plane, and (C) below the annulus.

FIG. 19 is an illustration of an orthogonal TVR valve 146 against illustrations of the location of native tissue, with IVC, PA, and the septal, posterior, and anterior leaflets, with an indicator of relative depths A-B-C referring to (A) above the annulus, (B) at or near the annular plane, and (C) below the annulus.

FIG. 20 is an illustration of a side view of a series showing how an anchor hook can progress from (i) a stowed position within a delivery catheter sheath/channel, (ii) to a subannular location while sheathed, (iii) to a subannular location with the anchor in an open position, and (iv) to a retracted position, according to the invention.

FIG. 21 is an illustration of a valve delivery process for an orthogonally delivered (side-delivered) valve, and shows a side view of a heart, with dashed circle showing a tricuspid region of interest.

FIG. 22 is an illustration of a valve delivery process for an orthogonally delivered (side-delivered) valve, and shows a side view of a guide wire 194 step of a multi-step delivery process.

FIG. 23 is an illustration of a valve delivery process for an orthogonally delivered (side-delivered) valve, and shows a side view of a catheter delivery 192 step of a multi-step delivery process, with a catheter 192 containing an orthogonally compressed valve 146 delivered via the IVC.

FIG. 24 is an illustration of a valve delivery process for an orthogonally delivered (side-delivered) valve 146, and shows a side view of a valve deployment step of a multi-step delivery process, with a catheter expelling an expanded uncompressed valve partially into the tricuspid annulus, with RVOT tab placed in the pulmonary artery right ventricular outflow tract (RVOT) anchoring area.

FIG. 25 is an illustration of a valve delivery process for an orthogonally delivered (side-delivered) valve, and shows a side view of a catheter delivery step of a multi-step delivery process, with a TVR valve 146 fully seated within the tricuspid annulus, RVOT tab, and proximal tab positioned to secure the valve, and subannular anchor devices delivered and inserted into position on or in the valve.

FIG. 26 is an illustration of an anchor hook delivery process, and shows a side view TVR valve fully seated within the tricuspid annulus, RVOT tab, and proximal tab positioned to secure the valve, and subannular anchor devices 110 extended subannularly to capture native tissue, e.g. annular ring, chordae, and/or leaflet.

FIG. 27 is an illustration of an anchor hook delivery process, and shows a side view of a TVR valve fully seated within the tricuspid annulus, RVOT tab, and proximal tab positioned to secure the valve, and subannular anchor devices 110 retracted after capture of native tissue, e.g. annular ring, chordae, and/or leaflet.

FIG. 28 is an illustration of side perspective view of a stowed or compressed anchor hook relative to native tissue during the anchoring-tissue capture process, with an indicator of relative depths A-B-C referring to (A) above the annulus.

FIG. 29 is an illustration of side perspective view of a partially expelled hook portion relative to native tissue during the anchoring-tissue capture process, with an indicator of relative depths A-B-C referring to (B) at or near the annular plane.

FIG. 30 is an illustration of side perspective view of an opened hook or bend portion of an anchor hook relative to native tissue during the anchoring-tissue capture process, with an indicator of relative depths A-B-C referring to (C) below the annulus.

FIG. 31 is an illustration of an anchor hook that has been adjusted from a compressed configuration, to an extended/opened configuration to capture native tissue.

FIG. 32 is an illustration of an anchor hook that has been adjusted from an open position to a retracted, and/or cinched configuration, with the sheath removed to allow the barbs to lodge into the channel wall.

FIG. 33 is an illustration of a side perspective view of an anchor delivery catheter delivering an anchor hook to a radiomarker spot on the valve collar, according to the invention.

FIG. 34 is an illustration of a side perspective view of an anchor hook deployed to a sub-annular position, according to the invention.

FIG. 35 is an illustration of a side perspective view of an anchor hook that has been deployed to a sub-annular position, and then retracted to capture the chordae and part of the anterior leaflet, according to the invention.

FIG. 36 is an illustration of a side perspective view a transcatheter delivery catheter that has access to the mitral valve from the IVC thru a trans-septal access to deliver an orthogonally deliverable (side-deliverable) mitral valve replacement prosthesis.

FIG. 37 is an illustration of a side perspective view a mitral valve embodiment having the anchor hooks deployed to an expanded position, according to the invention.

FIG. 38 is an illustration of a side perspective view a mitral valve embodiment having the anchor hooks compressed and/or cinched to capture native tissue, according to the invention.

FIG. 39 is an illustration of one embodiment of an anchor hook according to the invention. FIG. 39 shows from the top, a proximal tether loop 152, a single diamond-shaped cell, a series of three anchoring tabs or barbs disposed along a central shaft portion, and a hook portion attached at a distal end of the central shaft portion, where the hook portion is shown in an extended configuration. The extend hook portion configuration allows the anchor hook to have a catheter sheath withdrawn, or have the hook portion expelled from a channel, and the shape memory aspect of the hook portion will curl as it is it expelled from the cylinder lumen. Following capture of the native tissue by the self-curling hook portion, the anchoring tabs or barbs can be exposed by withdrawing a sheath further or expelling the device further out of the channel. The anchoring tabs or barbs can be pushed into native tissue, pushed into an outer polyester covering, or both, to further secure the valve within the native annulus.

FIG. 40 is an illustration of one embodiment of an anchor hook disposed within a delivery catheter that extends through an anchor channel in the valve body to a subannular tissue-capture position, according to the invention. The anchoring tabs or barbs and the hook portion are initially compressed against the shaft portion when within the delivery catheter. When the delivery catheter is advanced thru an anchor channel to a subannular position, an elongated pusher cable that is attached to a proximal end of the shaft portion unsheathes the anchor hook and expands the anchoring tabs or barbs and the hook portion to a heat-set shape-memory configuration.

FIG. 41 is an illustration of one embodiment of an anchor hook released from the delivery catheter allowing the shape-memory material to expand with anchoring tabs or barbs extending laterally, and hook portion extending away from the shaft portion, according to the invention. With the hook portion in a position to capture a leaflet and/or chordae tendinea, the pusher cable is then pulled in a proximal direction so that the hook portion pulls the captured tissue against the bottom of the valve body or against the annular ring tissue.

FIG. 42 is an illustration of one embodiment of an anchor hook partially pulled back into the anchor channel with anchoring tabs or barbs compressed into the lumen of the anchor channel, and lower shaft portion and hook portion remaining outside of the anchor channel for capture and securement/anchoring of native tissue to the valve body, according to the invention.

Pulling the pusher cable also draws the tabs/barbs into the anchor channel, where the channel is narrower than the extended radius of the tabs/barbs. This causes the tabs/barbs to partially fold toward the shaft portion, and create a tensioning force with each tab/barb pressing against the interior surface of the channel. Where the channel is a mesh or braid, the tabs/barbs are forced into the channel wall. The direction of the barb also inhibits distal movement of the anchor shaft, i.e. inhibits movement of the anchor away from the valve body.

Retrievability

The retrievability of the anchor hook originates from the ability of the delivery catheter to slide over the shaft portion while the tabs/barbs are engaging the channel wall, and to flatten the tabs/barbs back towards or against the shaft portion, thus disengaging the tabs/barbs from the channel interior wall. Once the tabs/barbs are disengaged, the delivery catheter is advanced distally to a subannular/ventricular position to release the hook portion from the captured native tissue. Once the hook portion is freed from the captured tissue, a tether that is attached to the anchor hook is pulled and folds the hook portion against the shaft portion. Once the hook portion is folded against the shaft portion, the entire anchor hook is then pulled into the delivery catheter and sheathed by the delivery catheter for withdrawal and/or redeployment of the anchor.

FIG. 43 is an illustration of a native mitral valve from a top perspective view above the annular plane from a transseptal access side view, and shows the A2 leaflet and P2 leaflet in a partially open position.

FIG. 44 is an illustration of a native mitral valve from a bottom perspective view below the annular plane from a P2 side view, and shows the A2 leaflet and P2 leaflet in a partially open position.

FIG. 45 is an illustration of a native mitral valve from a bottom perspective view below the annular plane from an A2 side view, and shows the A2 leaflet and P2 leaflet in a partially open position.

FIG. 46 is an illustration of a prosthetic transcatheter heart valve from a plan or side view, and shows a pair of anchor hooks, each disposed within an anchor channel on the exterior surface of the valve body. A first anchor hook in an exterior channel is shown with hook portion extended to capture a P2 mitral leaflet, and a second anchor hook in an exterior channel is shown with hook portion extended to capture a A2 mitral leaflet.

The anchoring tabs or barbs and the hook portion are initially compressed against the shaft portion when within the delivery catheter. When the delivery catheter is advanced thru an anchor channel to a subannular position, where an elongated pusher cable that is attached to a proximal end of the shaft portion unsheathes the anchor hook and expands the anchoring tabs or barbs and the hook portion to a heat-set shape-memory configuration. With the hook portion in a position to capture an A2 or P2 leaflet and/or chordae tendinea, the pusher cable is then pulled in a proximal direction so that the hook portion pulls the captured tissue against the bottom of the valve body or against the annular ring tissue.

Pulling the pusher cable also draws the tabs/barbs into the anchor channel, where the channel is narrower than the extended radius of the tabs/barbs. This causes the tabs/barbs to partially fold toward the shaft portion, and create a tensioning force with each tab/barb pressing against the interior surface of the channel. Where the channel is a mesh or braid, the tabs/barbs are forced into the channel wall.

The retrievability of the anchor hook originates from the ability of the delivery catheter to slide over the shaft portion while the tabs/barbs are engaging the channel wall, and to flatten the tabs/barbs back towards or against the shaft portion, thus disengaging the tabs/barbs from the channel interior wall. Once the tabs/barbs are disengaged, the delivery catheter is advanced distally to a subannular/ventricular position to release the hook portion from the captured native tissue. Once the hook portion is freed from the captured tissue, a tether that is attached to the anchor hook is pulled and folds the hook portion against the shaft portion. Once the hook portion is folded against the shaft portion, the entire anchor hook is then pulled into the delivery catheter and sheathed by the delivery catheter for withdrawal and/or redeployment of the anchor.

FIG. 47 is an illustration of a prosthetic transcatheter heart valve from a plan or side view, and shows a pair of anchor hooks, each disposed within an anchor channel within the cylinder of the valve body. A first anchor hook is shown with hook portion extended to capture a P2 mitral leaflet, and a second anchor hook is shown with hook portion extended to capture a A2 mitral leaflet.

FIG. 48 is an illustration of an anchor in a stowed or compressed delivery position.

FIG. 49 is an illustration of an anchor in an expanded deployed position.

FIG. 50 is an illustration of an embodiment of a bare metal anchor element 110, according to the invention.

FIG. 51 is an illustration of an embodiment of an anchor element having a polyester cover 174 for in-growth along the shank of the anchor, according to the invention.

FIG. 52 is an illustration of an embodiment of a split shank 140 anchor element having a polyester cover 174 along the split shank of the anchor, according to the invention.

FIG. 53 is an illustration of an embodiment of a split shank anchor element having a bare metal split shank and a polyester cover 174 on the bend or hook portion of the of the anchor, according to the invention.

FIG. 54 is an illustration of an embodiment of a split shank anchor element having a bare metal split shank and a polyester cover on the bend or hook portion of the of the anchor, according to the invention.

FIG. 55 is an illustration of a side perspective view of an orthogonally deliverable transcatheter heart valve 146 with external anchor channel(s) positioned on the exterior of the valve, and extending from cuff/collar along the outer side surface of the valve body to the subannular/lower side, with distal right ventricular outflow tract (RVOT) tab, and proximal tab also shown, according to the invention.

FIG. 56 is an illustration of a side perspective view of a channel 122 having a mesh or tissue channel cover 174. This allows delivery to effectively puncture the mesh and create a substrate to encourage in-growth.

FIG. 57 is an illustration of varying diameter sizes of the channel(s).

FIG. 58 is an illustration of varying channel length(s) of the channel(s).

FIG. 59 is an illustration of a side perspective view of a preferred embodiment of a channel and shows braided polyethylene as material for the channel.

FIG. 60 is an illustration of a side perspective view of a preferred embodiment of a channel and shows tissue as material for the channel.

FIG. 61 is an illustration of a side perspective view of a preferred embodiment of a channel and shows expanded polytetrafluoroethylene (ePTFE), as material for the channel.

FIG. 62 is an illustration of a side perspective view of a preferred embodiment of a channel and shows Nitinol® tube or stent, as material for the channel.

FIG. 63 is an illustration of radio-opaque marker 164 locations on a channel, and specifically a top ring location. Material choices for marker 164, according to the imaging modality that it could be used with, e.g. metal marker contrasts well with surrounding valve material under fluoro.

FIG. 64 is an illustration of radio-opaque marker locations on a channel, and specifically top and bottom ring locations.

FIG. 65 is an illustration of radio-opaque marker locations on a channel, and specifically top and bottom alignment dot locations.

FIG. 66 is an illustration of radio-opaque marker locations on a channel, and specifically a side strip(s) location.

FIG. 67 is an illustration of radio-opaque marker locations on a channel, and specifically a mid-band location.

FIG. 68 is an illustration of a side view of a channel-less anchor deployment system with a tunneling catheter 199 having a guide rod, a compressed tether lock, a compressed subannular anchor 110, disposed in a compressed configuration within the catheter 120, according to the invention. This system enables use of the anchor directly through the body of the valve, without requiring a channel. This anchoring system could be used with any valve, not just one that has channels.

FIG. 69 is an illustration of a side view of a channel-less anchor deployment system with a tunneling catheter having a guide rod, a compressed tether lock, a partially expelled, partially uncompressed subannular anchor, according to the invention.

FIG. 70 is an illustration of a side view of a channel-less anchor deployment system with a tunneling catheter having an uncompressed expanded tether lock 155, and an uncompressed subannular anchor 110, according to the invention.

FIG. 71 is an illustration of a side perspective view of an orthogonally deliverable transcatheter heart valve with channel-less pre-determined anchor pathway(s) extending from cuff/collar through the valve body to the subannular/lower side, and distal right ventricular outflow tract (RVOT) tab, a proximal tab according to the invention according to the invention, with anchor delivery catheter, having subannular anchor connected by flexible tether to expandable tether lock, prior to cinching the lock down onto the collar surface and the tab against a lower portion of the valve body.

FIG. 72 is an illustration of a side perspective view of an orthogonally deliverable transcatheter heart valve with channel-less pre-determined anchor pathway(s) extending from cuff/collar through the valve body to the subannular/lower side, and distal right ventricular outflow tract (RVOT) tab, a proximal tab according to the invention according to the invention, with anchor delivery catheter, having subannular anchor connected by flexible tether to expandable tether lock, after cinching the lock down onto the collar surface and the tab against a lower portion of the valve body.

FIG. 73 is an illustration of a side view of a tether lock that is compressed within a delivery sheath (catheter), with the tether lock having a central aperture, with the braided tether threaded thru the central aperture of the tether lock so that the tether lock can slide along the tether.

FIG. 74 is an illustration of a side view of a tether lock that is released by withdrawal of the sheath into an expanded, uncompressed configuration, with the expanded tether lock having a central aperture, and with the braided tether threaded thru the central aperture of the tether lock, and the central aperture having one or more locking teeth to tighten onto the tether and prevent further sliding along the tether. The locking teeth can be a curved, one-way type of pawl or tooth, or they may be piercing teeth that engage the tether when the tether lock is expanded.

FIG. 75 is an illustration of a cross-sectional side view of a tether lock that is released by withdrawal of the sheath into an expanded, uncompressed configuration, with the expanded tether lock having a central aperture, and the central aperture having one or more locking teeth to tighten onto the tether and prevent further sliding along the tether. The locking teeth can be a curved, one-way type of pawl or tooth, or they may be piercing teeth that engage the tether when the tether lock is expanded.

FIG. 76 is an illustration of another preferred embodiment of the invention and shows a compressible valve having a P anchor (near posterior leaflet) and an A anchor (near anterior leaflet), with the tissue anchor loops attached to flexible elongated straps or rods 112 similar to a cable tie, the flexible elongated strap having an attached anchor lock 155 that engages with a section of the strap having teeth, the anchor lock forming an encircling head with a pawl in the head that engages the teeth of the strap, such that when the anchor lock/head slides down the flexible elongated strap, the anchor lock/head is locked into place when the pawl prevents the anchor lock from sliding up the strap.

FIG. 77 is an illustration of a side view of a tissue anchor loop attached to a strap with anchor lock slid into a lower, locked position.

FIG. 78 is an illustration of a side perspective view towards a septal leaflet side of a tricuspid valve replacement with an upper collar attached to a body portion, with an RVOT tab, a proximal tab, a P anchor and an A anchor, with anchor locks slid down into a lower locking position.

FIG. 79 is an illustration of a side perspective view from a septal leaflet side of a tricuspid valve replacement with an upper collar attached to a body portion, with an RVOT tab, a proximal tab, a P anchor and an A anchor, with anchor locks slid down into a lower locking position.

FIG. 80 is an illustration of a top view of a tricuspid valve replacement with an upper collar attached to a body portion, with an RVOT tab, a proximal tab, a P anchor and an A anchor, with anchor locks slid down into a lower locking position.

FIG. 81 is an illustration of a side perspective view from above a septal leaflet side of a tricuspid valve replacement with an upper collar attached to a body portion, with an RVOT tab, a proximal tab, central flow control element (tri-leaflet valve), an S anchor (anchor near septal leaflet) and a P-S anchor (anchor near postero-septal leaflet commissure), with anchor locks slid down into a lower locking position.

FIG. 82 is an illustration of a top view of a three-anchor tricuspid valve replacement with an upper collar attached to a body portion, with an RVOT tab, a proximal tab, central flow control element (tri-leaflet valve), an S anchor (anchor near septal leaflet), a P anchor (anchor near posterior leaflet), and an A anchor (near anterior leaflet), with anchor locks slid down into a lower locking position.

FIG. 83 is an illustration of a top view of a four-anchor tricuspid valve replacement with an upper collar attached to a body portion, with an RVOT tab, a proximal tab, central flow control element (tri-leaflet valve), an S anchor, a P anchor, a P-S anchor, and an A anchor, with anchor locks slid down into a lower locking position.

FIG. 84 is an illustration of a side view of a series showing how an anchor can progress from (i) a stowed position within a delivery catheter sheath, (ii) an extended anchor position, (iii) an extended open position, (iv) a retracted position, and (v) a locked position, with an indicator of relative depths A-B-C referring to (A) above the annulus, (B) at or near the annular plane, and (C) below the annulus, according to the invention.

FIGS. 85A-85F are illustrations of side perspective view of the relation of the anchor(s) to native tissue during the anchoring-tissue capture process, with an indicator of relative depths A-B-C referring to (A) above the annulus, (B) at or near the annular plane, and (C) below the annulus, with anchor configurations including (a) compressed shown in FIG. 85A, (b) extended shown in FIG. 85B, (c) opened shown in FIG. 85C, (d) retracted shown in FIG. 85D, (e) locked shown in FIG. 85E, and (f) trimmed shown in FIG. 85F, according to the invention.

FIG. 86 is an illustration of a side view of an orthogonally compressed valve 146 within a valve delivery catheter 192, with pre-attached folded over elongated straps and anchor locks and with advancement (towing) wire 196 attached to the RVOT tab 166 to pull the valve out of the sheath by applying force to the distal end, according to the invention.

FIG. 87 is an illustration of a side view of a valve 146 partially expelled from the delivery catheter by the advancement (towing) wire, with pre-attached anchor 110 having folded over elongated straps and anchor locks, according to the invention.

FIG. 88 is an illustration of a side view of a fully released valve 146, with pre-attached elongated straps and anchor locks 110 released from the catheter sheath 192 and in ready position for anchor deployment and tissue capture, for the valve 146 having distal tab 166, and proximal tab 168, according to the invention.

FIG. 89 is an illustration of a side perspective view of an anchor delivery catheter delivering an anchor to a radio-marker spot on the valve collar, according to the invention.

FIG. 90 is an illustration of a side perspective view of an anchor deployed to a sub-annular position, and a tether lock mounted on the tether above the valve collar ready for the tissue cinching step, according to the invention.

FIG. 91 is an illustration of a side perspective view of an anchor deployed to a sub-annular position, retracted to capture the chordae and part of the anterior leaflet, with the tether lock slid down the tether to the valve collar to lock the anchor and cinch the native tissue, according to the invention.

FIGS. 92A-92G are illustrations of a variety of anchor loops and tissue capture structures, according to the present invention.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed:

1. An anchoring system for a transcatheter prosthetic heart valve, the anchoring system comprising:
    an anchor channel of the transcatheter prosthetic heart valve, an interior surface of the anchor channel defining a lumen;
    a delivery catheter having an outer diameter and having a lumen extending therethrough, at least a portion of the delivery catheter configured to be advanced though the lumen of the anchor channel, the outer diameter of the delivery catheter being smaller than an internal diameter of the lumen of the anchor channel;
    an anchor hook configured to be disposed within a distal end of the lumen of the delivery catheter and having:
        an elongated shaft portion having a proximal end that forms a proximal tether loop,
        a plurality of anchoring tabs or barbs disposed along the elongated shaft portion and biased to an expanded configuration in which the tabs or barbs extend away from a central axis of the elongated shaft portion to a radius from the central axis larger than the inner diameter of the anchor channel, and movable to a closed or compressed configuration in which the tabs or barbs are folded towards the central axis of the elongated shaft portion to a radius from the central axis smaller than the inner diameter of the anchor channel, and
        a hook portion at a distal end of the elongated shaft portion, the hook portion configured to be disposed within the lumen of the delivery catheter in a compressed configuration in which the hook portion is folded towards the central axis of the elongated shaft portion and biased towards an expanded configuration in which the hook portion extends away from the central axis of the elongated shaft portion; and an elongated pusher releasably engageable with the proximal end of the elongated shaft portion and configured to extend proximally through the delivery catheter,
    a tether coupled to a tether mount of the hook portion and extending proximally through the proximal tether loop and the lumen of the delivery catheter,
    the anchoring system being operable to have (i) the distal end of the delivery catheter disposed within the lumen of the anchor channel, (ii) the anchor hook pushed in a distal direction out of the delivery catheter and through the anchor channel, via the elongated pusher, to a position in which the hook portion extends out of the anchor channel and transitions to its expanded configuration, and (iii) the anchoring tabs or barbs engage the interior surface of the anchor channel to limit movement of the anchor hook in the distal direction,
    the anchoring system being further operable to retrieve the anchor hook by application of a proximal force on the tether to urge the hook portion from its expanded configuration to its compressed configuration and to withdraw the anchor hook in a proximal direction into the anchor channel.

2. The anchoring system of claim 1, wherein the delivery catheter is configured to extend through a valve body portion of the transcatheter prosthetic heart valve via the anchor channel, the anchor channel being integrated into or attached to one of an interior surface or an exterior surface of the valve body portion of the transcatheter prosthetic heart valve.

3. The anchoring system of claim 1, wherein the elongated shaft portion is selected from a single elongated member with the anchoring tabs or barbs extending away from the elongated member, or a chain of diamond-shaped cells with the anchoring tabs or barbs extending from lateral points of the diamond-shaped cells.

4. The anchoring system of claim 1, wherein the hook portion is one of a single diamond-shaped cell or a diamond-shaped cell with one or more anchoring tabs or barbs extending from lateral points of the diamond-shaped cell.

5. The anchoring system of claim 1, wherein the anchor hook is a first anchor hook, the delivery catheter is a first delivery catheter, the anchor channel is a first anchor channel, and the anchoring system further comprising:
- a second anchor hook disposed in a distal end of a second delivery catheter; and
- a second anchor channel of the transcatheter prosthetic heart valve, an interior surface of the second anchor channel defining a lumen, at least a portion of the second delivery catheter configured to be advanced through the lumen of the second anchor channel.

6. The anchoring system of claim 1, wherein at least a portion of the anchor hook is configured to be compressed within the anchor channel,
- wherein the anchor channel extends through a valve body portion of the transcatheter prosthetic heart valve vertically or at an angle up to 45 degrees from vertical, and
- wherein vertical is parallel to a central atrial-to-ventricle axis of the transcatheter prosthetic heart valve.

7. The anchoring system of claim 1, wherein the elongated shaft has between 2-6 tabs or barbs configured to engage the interior surface of the anchor channel when the anchor hook is distal to the delivery catheter.

8. The anchoring system of claim 1, wherein the anchoring system is configured such that:
- the elongated pusher is configured to push, in response to a distally-directed force exerted on the elongated pusher and when the distal end of the delivery catheter is disposed within the lumen of the anchor channel, the anchor hook distally out of the delivery catheter and the anchor channel allowing the hook portion to transition to the expanded configuration to capture native leaflet tissue or native chordae tendineae within or on the hook portion of the anchor hook, and
- the elongated pusher is configured to pull, in response to a proximally-directed force exerted on the elongated pusher and after the hook portion transitions to the expanded configuration, the anchor hook proximally into the anchoring channel and causes the hook portion to press the native leaflet tissue or native chordae tendineae against a subannular portion of the transcatheter prosthetic heart valve or a subannular surface of a native annulus of a heart.

9. The anchoring system of claim 8, wherein the anchoring system is further configured such that exerting the proximally-directed force on the elongated pusher pulls the anchor hook proximally into the anchoring channel and causes the tabs or barbs in their expanded configuration to be at least partially compressed and pulled into the anchor channel such that the tabs or barbs press against the interior surface of the anchor channel creating a tension force therebetween operable to limit movement of at least the hook portion in the distal direction.

* * * * *